US010582890B2

(12) United States Patent
Bandyopadhyay et al.

(10) Patent No.: US 10,582,890 B2
(45) Date of Patent: Mar. 10, 2020

(54) VISUALIZING, SCORING, RECORDING, AND ANALYZING SLEEP DATA AND HYPNOGRAMS

(71) Applicant: Awarables, Inc., Potomac, MD (US)

(72) Inventors: Amrit Bandyopadhyay, Washington, DC (US); Gilmer Blankenship, Washington, DC (US); Madhvi Upender, Potomac, MD (US); Raghu Upender, Potomac, MD (US)

(73) Assignee: Awarables Inc., Baltimore, MD (US)

( * ) Notice: Subject to any disclaimer, the term of this patent is extended or adjusted under 35 U.S.C. 154(b) by 0 days.

(21) Appl. No.: 15/249,032

(22) Filed: Aug. 26, 2016

(65) Prior Publication Data

US 2017/0055899 A1 Mar. 2, 2017

Related U.S. Application Data

(60) Provisional application No. 62/211,344, filed on Aug. 28, 2015, provisional application No. 62/211,261, filed on Aug. 28, 2015.

(51) Int. Cl.
*A61B 5/00* (2006.01)
*A61B 5/0408* (2006.01)
(Continued)

(52) U.S. Cl.
CPC ............ *A61B 5/4815* (2013.01); *A61B 5/002* (2013.01); *A61B 5/02055* (2013.01);
(Continued)

(58) Field of Classification Search
CPC ... A61B 5/4815; A61B 5/002; A61B 5/02055; A61B 5/04085; A61B 5/0432;
(Continued)

(56) References Cited

U.S. PATENT DOCUMENTS 4,999,772 A 3/1991 Bowman et al.
5,259,390 A 11/1993 Maclean
(Continued)

FOREIGN PATENT DOCUMENTS

DE 102005048496 4/2007
JP 2005/152310 6/2005
(Continued)

OTHER PUBLICATIONS

ChuDuc et al., "Effect of Calculation Algorithm on Heart Rate Variability by Chaos Theory", International Journal of Electronics and Electrical Engineering 2013, 1(3):145-148.
(Continued)

*Primary Examiner* — Carl H Layno
*Assistant Examiner* — Michael J Lau
(74) *Attorney, Agent, or Firm* — Fish & Richardson P.C.

(57) ABSTRACT

Methods, systems, and apparatus, including computer programs encoded on a computer storage medium, for visualizing, scoring, recording, and analyzing sleep data and hypnograms. In some implementations, a method includes generating and providing a representation of sleep stages that includes a sequence of elements indicating a progression of the sleep stages over time during a sleep session. In some implementations, a method includes generating and providing one or more scores based on analysis of the sleep session. In some implementations, a wearable body data recorder includes a plurality of sensors and is configured to measure and process sensor data obtained during a sleep session of a subject.

23 Claims, 13 Drawing Sheets

(51) Int. Cl.
*A61B 5/0432* (2006.01)
*A61B 7/00* (2006.01)
*A61B 5/0205* (2006.01)
*A61B 5/11* (2006.01)
*A61B 5/01* (2006.01)
*A61B 5/0245* (2006.01)

(52) U.S. Cl.
CPC ........ *A61B 5/0432* (2013.01); *A61B 5/04085* (2013.01); *A61B 5/11* (2013.01); *A61B 5/4809* (2013.01); *A61B 5/4812* (2013.01); *A61B 5/4818* (2013.01); *A61B 5/6804* (2013.01); *A61B 5/743* (2013.01); *A61B 7/003* (2013.01); *A61B 5/01* (2013.01); *A61B 5/0245* (2013.01); *A61B 5/742* (2013.01); *A61B 2503/12* (2013.01); *A61B 2503/42* (2013.01); *A61B 2505/09* (2013.01); *A61B 2560/0242* (2013.01)

(58) Field of Classification Search
CPC ....... A61B 5/11; A61B 5/4809; A61B 5/4812; A61B 5/4818; A61B 5/6804; A61B 5/743; A61B 7/003
USPC ......................................... 600/300
See application file for complete search history.

(56) References Cited

U.S. PATENT DOCUMENTS

| | | |
|---|---|---|
| 5,280,791 A | 1/1994 | Lavie |
| 5,732,696 A | 3/1998 | Rapoport et al. |
| 6,241,686 B1 | 6/2001 | Balkin et al. |
| 6,878,121 B2 | 4/2005 | Krausman et al. |
| 7,324,845 B2 | 1/2008 | Mietus et al. |
| 2004/0073098 A1 | 4/2004 | Geva et al. |
| 2004/0230105 A1 | 11/2004 | Amir et al. |
| 2004/0230398 A1* | 11/2004 | Okada ................ A61B 5/02055 702/182 |
| 2004/0254493 A1 | 12/2004 | Chervin et al. |
| 2005/0115561 A1 | 6/2005 | Stahmann et al. |
| 2005/0119285 A1* | 6/2005 | Matos ................ A61K 31/454 514/263.22 |
| 2005/0143617 A1 | 6/2005 | Auphan |
| 2006/0060198 A1 | 3/2006 | Aylsworth et al. |
| 2006/0111635 A1 | 5/2006 | Todros et al. |
| 2006/0149144 A1 | 7/2006 | Lynn et al. |
| 2006/0235315 A1* | 10/2006 | Akselrod ........... A61B 5/02405 600/509 |
| 2007/0016095 A1* | 1/2007 | Low ...................... A61B 5/048 600/544 |
| 2007/0129769 A1* | 6/2007 | Bourget ............... A61B 5/0002 607/45 |
| 2009/0005652 A1* | 1/2009 | Kurtz ...................... A61B 5/00 600/300 |
| 2009/0292215 A1 | 11/2009 | Todros et al. |
| 2010/0204334 A1* | 8/2010 | Greco ................ A61K 9/0043 514/618 |
| 2010/0240982 A1* | 9/2010 | Westbrook ............ A61B 5/087 600/391 |
| 2011/0015495 A1* | 1/2011 | Dothie .................. G16H 10/60 600/300 |
| 2012/0253220 A1 | 10/2012 | Rai et al. |
| 2012/0323085 A1* | 12/2012 | Takeda ................ A61B 5/4815 600/300 |
| 2013/0310712 A1* | 11/2013 | Kanemitsu .............. A61B 5/11 600/595 |
| 2013/0338446 A1* | 12/2013 | Van Vugt ............. A61B 5/4806 600/300 |
| 2014/0088378 A1* | 3/2014 | Muzet ................ A61B 5/02125 600/301 |
| 2014/0222720 A1 | 8/2014 | Hames et al. |
| 2015/0109124 A1 | 4/2015 | He et al. |
| 2015/0164238 A1* | 6/2015 | Benson .................. G16H 50/30 340/540 |
| 2015/0238139 A1* | 8/2015 | Raskin ................ A61B 5/4866 600/595 |
| 2016/0151603 A1* | 6/2016 | Shouldice ................ H04R 3/00 600/28 |
| 2016/0310696 A1 | 10/2016 | Fonseca et al. |

FOREIGN PATENT DOCUMENTS

| | | |
|---|---|---|
| JP | 2007/195823 | 8/2007 |
| WO | WO 01/43804 | 6/2001 |
| WO | WO 02/100267 | 12/2002 |
| WO | WO 2004/026133 | 4/2004 |
| WO | WO 2006/002338 | 1/2006 |
| WO | WO 2008/132736 | 11/2008 |
| WO | WO 2009/144598 | 12/2009 |
| WO | WO 2012/112186 | 8/2012 |
| WO | WO 2012/153263 | 11/2012 |
| WO | WO 2013/054712 | 4/2013 |
| WO | WO 2015/006364 | 1/2015 |
| WO | WO 2015/103558 | 7/2015 |

OTHER PUBLICATIONS

Krstacic et al., "The Chaos Theory and Non-linear Dynamics in Heart Rate Variability in Patients with Heart Failure", Computers n Cardiology 2008, 35:957-959.
Liang et al., "A rule-based automatic sleep staging method", Journal of Neuroscience Methods 2012, 205:169-176.
Ritterband et al., "A Behavior Change Model for Internet Interventions", Ann Behav Med. 2009, 38(1):18-27.
Stein et al., "Heart rate variability, sleep and sleep disorders", Sleep Medicine Reviews 2012, 16:47-66.
Cheng-Pin et al., "An RFID tag system-on-chip with wireless ECG monitoring for intelligent healthcare systems," The Effect of Applied Compressive Loading on Tissue-Engineered Cartilage Constructs Cultured With TGF-BETA3, IEEE, Jul. 2013, pp. 5489-5492.
International Search Report and Written Opinion in International Application No. PCT/US2016/049101, dated Nov. 25, 2016, 17 pages.
International Search Report and Written Opinion in International Application No. PCT/US2016/049104, dated Dec. 2, 2016, 18 pages.
Karlen et al., "Sleep antd Wake Classification With ECG and Respiratory Effort Signals," IEEE Transactions on Biomedical Circuits and Systems, IEEE, Apr. 2009, 3(2):71-78.
USPTO Non-Final Office Action issued in related U.S. Appl. No. 15/249,108, dated Jun. 27, 2017, 12 pages.
USPTO Non-Final Office Action issued in related U.S. Appl. No. 15/249,108, dated Mar. 3, 2017, 11 pages.

* cited by examiner

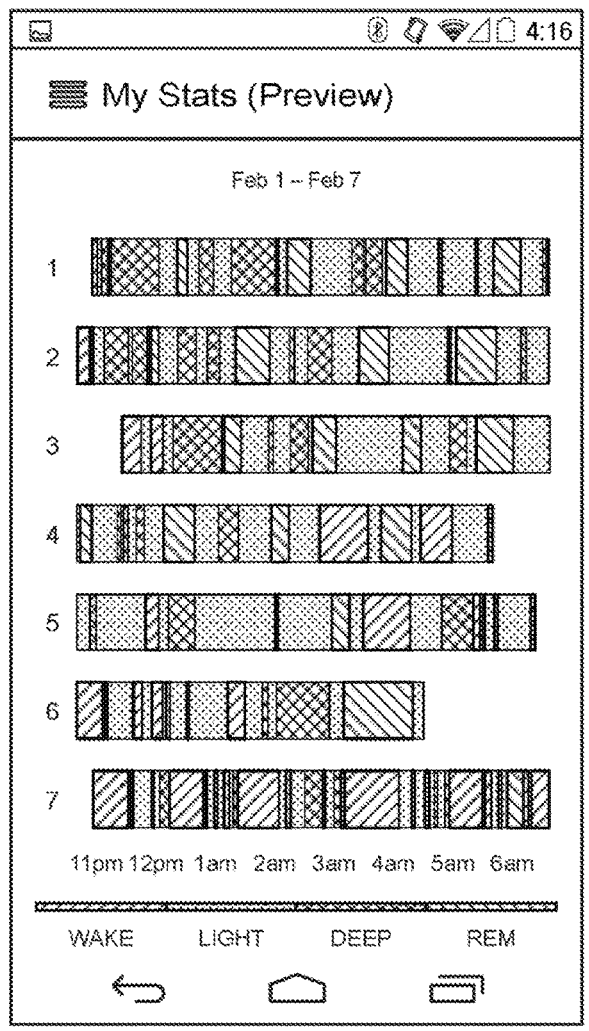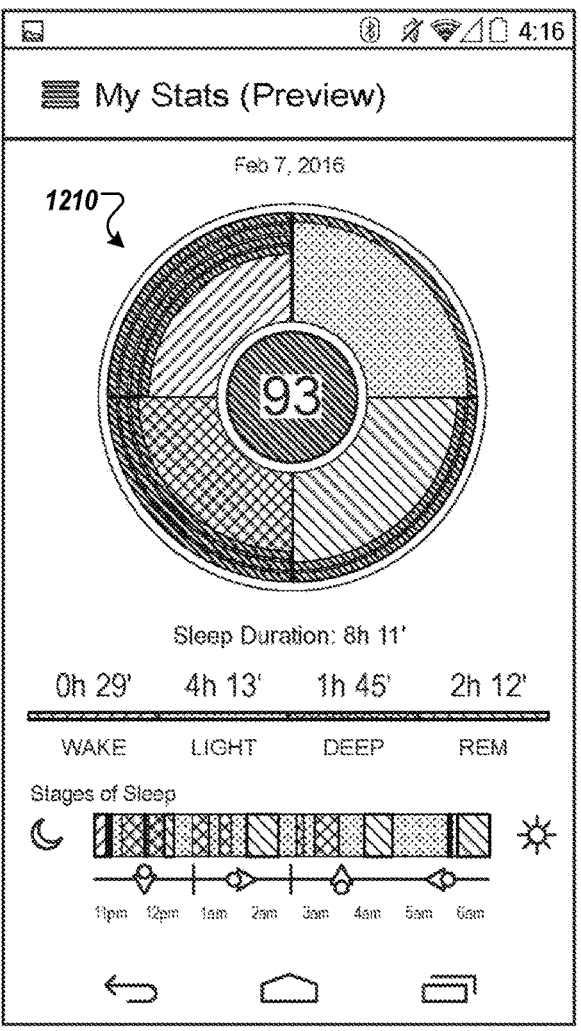
FIG. 11
FIG. 12

VISUALIZING, SCORING, RECORDING, AND ANALYZING SLEEP DATA AND HYPNOGRAMS

CROSS-REFERENCE TO RELATED APPLICATIONS

This application claims priority to U.S. Provisional Application No. 62/211,344, filed on Aug. 28, 2015, and U.S. Provisional Application No. 62/211,261, filed on Aug. 28, 2015. The entire contents of U.S. Provisional Application Nos. 62/211,344 and 62/211,261 are incorporated herein by reference.

GOVERNMENT RIGHTS

The subject matter disclosed herein was made with U.S. government support under the award/contract/grant number 1416220, awarded by the National Science Foundation, and W81XWH-15-C-0025, awarded by the Department of Defense. The U.S. government may have certain rights in the subject matter disclosed herein.

TECHNICAL FIELD

The present disclosure relates to systems to monitor and analyze the quality and quantity of a person's sleep.

BACKGROUND

A person's sleep can be assessed with a polysomnogram (PSG), which is a multi-channel procedure carried out in a sleep laboratory. Typically, the procedure requires labor-intensive technician support, resulting in an expensive process. The studies are typically performed for a single night in a Sleep Laboratory and sometimes also during the day to study daytime sleepiness, e.g., with a Multiple Sleep Latency Test (MSLT). The results of the sleep study are primarily (i) indices related to apnea events, such as an Apnea-Hypopnea Index (AHI), and (ii) sleep staging outputs that indicate the stages of sleep that occurred.

Sleep stages reported as a result of a sleep study often follow either the Rechtschaffen and Kales (R&K) scoring system or the American Academy of Sleep Medicine (AASM) system established in 2007. In the R&K system the stages of sleep are S1, S2, S3, S4, REM (Rapid Eye Movement), and Wake. In the AASM format, S3 and S4 were combined into a single stage, N3, with the stages of sleep being N1, N2, N3, REM, and Wake. However, a typical PSG requires multiple EEG (electroencephalogram) channels, an EOG (electrooculogram), an EKG (electrocardiogram), an EMG (electromyography), and analysis of data from other sensors. As a result, a PSG can be a rather invasive procedure and is typically administered for only a single session or two.

SUMMARY

Disclosed herein are methods and systems for analytical visualization, parametric aggregation, and intuitive scoring for sleep data. A novel combination of sensors to record sleep data is also disclosed. Methods and systems for logging additional sleep data including subjective evaluations and daily habits and correlating multiple types of sleep data are described. In some implementations, a computer-implemented method may include obtaining hypnograms and annotations for one or more nights of sleep for a subject, generating graphical representations of these hypnograms and annotations, extracting parameters to describe the sleep signature for the subject, and computing scores for the quality and quantity of sleep for each sleep session and the overall subject. In some implementations, the sleep visualization, statistical parameter extraction and scoring is performed for a plurality of subjects. In other implementations, this sleep data is further correlated with subjective evaluations and habit diary entries, which can be logged via a computer system.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to limitations that solve any or all disadvantages noted in any part of this disclosure.

Common techniques for analyzing sleep often fail to provide accurate, understandable information about the stages and quality of sleep that has occurred. Many systems are unable to provide measures of key aspects of sleep quality. Manually derived sleep analysis can also be inconsistent and inaccurate. The techniques disclosed involve a computerized process for analyzing sleep characteristics that can provide better consistency and accuracy than previous approaches and manual analysis.

Prior devices for measuring sleep data have not included sufficient sensing capabilities to measure a patient's body data and environmental factors that affect sleep. Prior devices are often bulky and uncomfortable, and interfere with a patient's normal sleep habits. This document describes a body data recorder that is small and includes a variety of sensors which can be comfortably worn to record sleep data over multiple sleep sessions. In some implementations, the body data recorder is at least partially integrated into a shirt that the patient wears during sleep. The shirt can include EKG contacts or other sensor elements, and a small device with additional sensors and a processing unit can be attached. Together, the shirt and associated device can measure, e.g., temperature, EKG signal, heartbeat, light levels, sound, movement, and/or other information that can be used to analyze the amount and quality of a subject's sleep.

In general, there is a lack of intuitive visualization mechanisms for the results of sleep studies. The current standard is a simple line graph showing sleep stage transitions based on PSG scoring by a technician. This graph is primarily viewed within the technician's scoring software platform during the scoring process. The lack of more a revealing visualization results in the low usage and limited analysis and application of sleep staging results. This lack of analysis is further compounded by the typically one night nature of the sleep laboratory, which is unlikely to accurately represent the average sleep pattern of the subject. This sleep staging sequence and other sleep characteristics (for one or more nights) is herein defined and referred to as the "sleep signature" for a subject. This signature is unique from subject to subject and from night to night. As such it can be a useful indicator of the character of a night's sleep.

For systems that have been developed to permit sleep monitoring for multiple nights, visualization and analytics can be used to derive and determine a comprehensive sleep signature for a subject by aggregating the results for multiple nights of sleep. These signatures can be also be determined across different subjects e.g., subjects with obstructive sleep apnea.

Subjective diaries of sleep schedules, daily habits and sleep satisfaction have traditionally been maintained on paper. Many clinicians believe them to be inaccurate. The diaries are often not completed in timely fashion and are subject to recall bias. There is, therefore, a need for computerized mechanisms to make such data easy to enter and store and to increase the data validity and accuracy. Additionally, there is also a need for methods to correlate these subjective entries and reported patient outcomes with quantitative measures of sleep quality, quantity, and related metrics. This could enable and automate the determination of causes of poor sleep in subjects, and recommendations of ways and steps to improve sleep.

In one general aspect, a method performed by one or more computing devices includes: accessing, by the one or more computing devices, data indicating sleep stages of a particular person during a sleep session; generating, by the one or more computing devices, data for a visual representation of the sleep stages of the sleep session, and the visual representation includes a ribbon having a sequence of elements indicating a progression of the sleep stages over time during the sleep session; and providing, by the one or more computing devices, the data for the visual representation for display on a display device.

Other embodiments of this aspect and the other aspects described herein include corresponding systems, apparatus, and computer programs, configured to perform the actions of the methods, encoded on computer storage devices. A system of one or more computing devices can be so configured by virtue of software, firmware, hardware, or a combination of them installed on the system that in operation cause the system to perform the actions. One or more computer programs can be so configured by virtue having instructions that, when executed by data processing apparatus, cause the apparatus to perform the actions.

This and other aspects may include one or more of the following features. For instance, in some implementations, the sequence of elements is a sequence of adjacent elements indicating different sleep stages over a continuous range of time during the sleep session.

In some implementations, the method includes accessing data indicating sleep stages of multiple different sleep sessions of the particular person. Generating the data for the visual representation includes generating data for a visual representation of the multiple different sleep sessions, and the visual representation includes, for each sleep session, a ribbon having a sequence of horizontal elements indicating a progression of the sleep stages over time during the sleep session.

In some implementations, the ribbons for the multiple sleep sessions are arranged in a column.

In some implementations, the ribbons for the multiple sleep sessions are horizontally aligned so that (i) a same horizontal position indicates a same time of day for each of the sleep sessions, or (ii) a same horizontal position indicates a start of each of the sleep sessions.

In some implementations, the number ribbons for sleep sessions displayed in the visual representation and horizontal alignment can be changed to view multiple sleep session sleep architectures or sleep signatures.

In some implementations, providing the data for the visual representation for display on a display device includes: displaying the ribbons representing the multiple sleep sessions on a user interface of an application of a mobile device; and displaying, in the user interface, one or more interactive controls that, when selected by a user of the mobile device, cause the user interface of the application to (i) adjust the horizontal alignment of the ribbons relative to each other, (ii) change the number of ribbons representing sleep sessions that are shown in the user interface, or (iii) change which sleep sessions are represented by ribbons in the user interface of the application.

In some implementations, the sequence of elements represents a sequence of segments of the sleep session, each segment representing an uninterrupted period that a single sleep stage occurred.

In some implementations, the elements are sized according to the respective durations of the segments corresponding to the elements, and each of the elements is color-coded to indicate the sleep stage of the corresponding segment.

In some implementations, the sequence of elements includes a set of contiguous rectangular elements that form rectangular ribbon, the boundaries between the rectangular elements representing transitions from one sleep stage to another, and the set of contiguous rectangular elements is ordered in sequence from left to right in the sequence that the corresponding segments occur in the sleep session.

In some implementations, the sleep stages include a wake stage, a rapid eye movement (REM) stage, and two or more different types of non-REM stages.

In some implementations, generating the data for the visual representation of the sleep stages includes generating data for a visual representation that includes indicators of events occurring during the sleep session, the indicators being aligned relative to the elements to indicate, with respect to the elements, times that the events occurred.

In some implementations, the indicators are indicators of sleep apnea events.

In some implementations, generating the data for the visual representation of the sleep stages includes generating data for a visual representation that includes, for each of one or more of the elements, a numerical representation of a duration of the sleep stage corresponding to the element.

In some implementations, accessing the data indicating the sleep stages includes: receiving the data at a user device from a server system over a network; and displaying the visual representation on a screen of the user device.

In some implementations, the user device is a mobile phone, and the visual representation is generated by a mobile application of the mobile phone.

In some implementations, the method includes receiving, by a user device, a short-range wireless signal from a body data recorder worn by the particular person, and the data indicating the sleep stages is determined based on the sensor data, and the visual representation is displayed by the user device.

In another general aspect, a method performed by one or more computing devices includes: accessing, by the one or more computing devices, sleep stage data generated from sensor data measured during a sleep session of a subject, the sleep stage data indicating periods of the sleep session and corresponding sleep stages during the periods; determining, by the one or more computing devices, one or more scores based on analysis of the sleep session; and providing, by the one or more computing devices, an indication of the determined one or more scores for display at a user device.

This and other aspects may include one or more of the following features. For instance, in some implementations, determining the one or more scores includes determining a sleep onset latency score indicating an amount of time between a wake stage and a first sleep stage that occurs after the wake stage.

In some implementations, determining the one or more scores includes determining a sleep onset latency score indicating an amount of time between a wake stage and a first sleep stage that occurs after the wake stage.

In some implementations, determining the one or more scores includes determining a total sleep time representing a total time the subject is in non-wake sleep stages during the sleep session.

In some implementations, determining the one or more scores includes determining, for each particular stage of multiple sleep stages, a stage duration score indicating an amount of time during the sleep session that the subject spent in the particular stage.

In some implementations, determining the one or more scores includes determining, for each particular stage of multiple sleep stages, one or more stage occurrence scores indicating (i) the number of stable occurrences of the particular sleep stage during the sleep session, and/or (ii) the number of transitions to the particular sleep stage from a different sleep stage during the sleep session or the number of transitions from the particular sleep stage to a different sleep stage during the sleep session.

In some implementations, a stable occurrence of a particular sleep stage is a segment of the sleep session that (i) the sleep stage data indicates corresponds to the particular sleep stage and (ii) has at least a minimum duration.

In some implementations, determining, for each of different pairs of sleep stages, a number of transitions between the two sleep stages in the pair.

In some implementations, determining the one or more scores includes determining, for each particular stage of multiple sleep stages, a longest segment for the particular sleep stage.

In some implementations, determining the one or more scores includes determining a number of events of a particular type, and durations of the events, that occurred during the sleep session, where the particular type of events is a snoring event or an apnea event.

In some implementations, determining the one or more scores includes: determining a sleep onset time, determining a final wake segment in the sleep session, and determining a Wake After Sleep Onset (WASO) score as a sum of all segment durations for segments designated as "wake" segments, excluding those before the sleep onset time and the final wake segment.

In some implementations, determining the one or more scores includes determining an awakenings score that indicates a number of segments scored as wake excluding segments before sleep onset and the final wake segment.

In some implementations, determining the one or more scores includes determining a cumulative sleep score based on a sum of durations of segments of the sleep session designated as REM stages and durations of segments designated as slow wave sleep segments.

In some implementations, determining the one or more scores includes determining a REM Score representing the architecture of a subject's REM stages.

In some implementations, the REM score is determined based on (i) a total duration of segments designated as REM stages during the sleep session and (ii) the longest stable REM segment during the sleep session.

In some implementations, the REM score is determined based on determining whether segments designated as REM stages have an increasing length as the sleep session progresses.

In some implementations, determining the one or more scores includes determining a slow wave sleep (SWS) score representing the architecture of a subject's deep sleep.

In some implementations, the SWS Score is determined based on (i) a total duration of segments designated as SWS stages during the sleep session and (ii) the longest stable SWS segment during the sleep session.

In some implementations, the SWS score is determined based on an amount of SWS sleep completed within the first four hours after sleep onset during the sleep session.

In some implementations, determining the one or more scores includes determining a general sleep score that is based at least in part on amounts of time spent awake during the sleep session relative to an amount of time spent sleeping during the sleep session.

In some implementations, the general score is determined as a geometric mean of a Wake After Sleep Onset score and Total Sleep Time score.

In some implementations, the Wake After Sleep Onset Score is a number that decays in a Gaussian trend as the time awake after sleep onset increase; and the Total Sleep Time score is based on an amount of sleep that occurred during the sleep session relative to a target amount of sleep.

In some implementations, the steps of the method are performed by an application running on the user device, and the user device is a mobile phone, tablet computer, wearable device, or other mobile processing device.

In some implementations, the steps of the method are performed by a remote computer system that is connected to a user device over a computer network, the remote computer system being configured to generate and provide information for display at the user device.

In some implementations, the sleep stage data is generated from sensor outputs of multiple sensors of a wearable body data recorder.

In some implementations, the method includes providing, by the one or more computing devices, a user interface of an application running on the user device.

In some implementations, providing, on the user interface of the application, one or more controls configured to receive, form a user of the user device, user input sleep data indicating habits of the user, lifestyle characteristics of the user, subjective feelings of the user, and/or a measure of sleep satisfaction of the user; and correlating, by the one or more computing devices, the user input sleep data with one or more sleep metrics or sensor data recorded during one or more sleep sessions of the user.

In some implementations, the method includes generating one or more scores based on timing of the user input sleep data with respect to one or more sleep sessions.

In some implementations, the method includes determining one or more patterns of relationships between the user input sleep data and sleep metrics over multiple sleep sessions.

In some implementations, the method includes providing, on the user interface of the application, a reaction time test to measure the user's reaction time following a sleep session.

In some implementations, the method includes correlating the results of the reaction time test with one or more sleep metrics, the reaction time test being administered at different times and after different sleep sessions; using the correlations of the results of the reaction time test with the one or more sleep metrics to determine one or more sleep scores for the user; and providing an indication of the determined one or more sleep scores for display by the user device.

In some implementations, the method includes analyzing sleep metrics determined for multiple sleep sessions to track sleep debt of the user; and generating data that indicating a likelihood of adverse outcomes using sleep architectures indicating patterns of sleep stages within a sleep session and scores for the sleep sessions.

In some implementations, the method includes analyzing sleep data to represent a sleep signature as a combination of measures aggregated according to their corresponding times of occurrence during sleep sessions, the measure include sleep metrics, sleep scores, sleep stage durations, and/or probability densities of sleep stages.

In another general aspect, a device includes: at least two EKG contacts to measure EKG signals of a subject during a sleep session; a processing module configured to move with the subject, the processing module comprising at least one processor and at least one data storage device; and one or more sensors, the one or more sensors being configured to detect a condition of the subject or an environment proximate to the subject. The processing module is configured to record sensor data during the sleep session of the subject, the sensor data indicating (i) EKG signals detected using the EKG contacts and (ii) the condition detected using the one or more sensors, the processing module being configured to record data indicating timing of the ambient condition relative to the EKG signals detected.

This and other aspects may include one or more of the following features. For instance, in some implementations, the device includes a wearable housing that houses the one or more sensors and the processing module, the housing being configured to receive the EKG signals detected through the EKG contacts when worn by the subject.

In some implementations, the device includes a battery; and a short-range wireless transceiver, and the device is configured to transmit the sensor data using the short-range transceiver. The device is configured to detect, record, and transmit the sensor data as a wireless and self-contained system.

In some implementations, the one or more sensors comprise a microphone, and the processing module is configured to record data indicating sounds detected by the microphone during the sleep session.

In some implementations, the processing module is configured to (i) detect apnea events of the subject based on signals detected by the microphone and (ii) store data indicating the apnea events.

In some implementations, the one or more sensors comprise a light sensor, and the processing module is configured to record ambient light levels detected by the light sensor during the sleep session.

In some implementations, the one or more sensors comprise a temperature sensor, and the processing module is configured to record temperatures detected by the temperature sensor during the sleep session.

In some implementations, the one or more sensors comprise a motion sensor, and the processing module is configured to record movement of the subject detected by the motion sensor during the sleep session.

In some implementations, the motion sensor includes at least one accelerometer.

In some implementations, the motion sensor includes at least one gyroscope.

In some implementations, the device includes a garment, and the at least two EKG contacts, the processing module, and the one or more sensors are coupled to the garment.

In some implementations, the garment is a shirt.

In some implementations, the at least two EKG contacts comprise an electrically-conductive polymer.

In some implementations, the EKG contacts are arranged in the garment to contact the pectoral muscles of a subject.

In some implementations, the device includes at least three EKG contacts.

In some implementations, the device includes a short-range wireless transceiver, and the device is configured to send, to a user device using the short-range wireless transceiver, (i) sensor data acquired by the one or more sensors and/or (ii) results of analysis of the sensor data performed by the processing module.

The details of one or more embodiments of the invention are set forth in the accompanying drawings and the description below. Other features and advantages of the invention will become apparent from the description, the drawings, and the claims.

BRIEF DESCRIPTION OF THE DRAWINGS

FIG. 11 is a diagram that illustrates a user interface of a mobile application showing hypnograms for a subject.

FIG. 12 is a diagram that illustrates a user interface of a mobile application showing indications of sleep scores for multiple aspects of sleep.

Like reference numbers and designations in the various drawings indicate like elements.

DETAILED DESCRIPTION

In the normal adult there are two main phases of sleep that alternate at about 90-minute intervals. Rapid eye movement (REM) sleep can be roughly described as a period when the brain is active and the body is immobile (except for eye movements, middle ear ossicles, and respiration). In non-rapid eye movement (NREM) sleep, the brain is less active but the body can move. NREM sleep is composed of four stages that are differentiated on the basis of EEG features. When healthy individuals first fall asleep, they enter Stage 1 (S1—sleep drowsiness) and then progress through Stages 2, 3, and 4 of NREM sleep. Stages 3 and 4 (S3, S4—deep sleep) are often called slow wave sleep or delta sleep because they are characterized by high amplitude, slow waves (delta waves) in the EEG. Slow wave sleep may last from a few minutes to an hour, depending on the person's age and prior sleep history, before reverting back to Stage 2 sleep. Usually after this, the first REM sleep period begins, lasting about 15-20 minutes and is followed by another NREM cycle. This alternating pattern continues throughout the night, but as the night progresses slow wave Stages 3 and 4 are less apparent and the periods of REM sleep grow longer. The plots in FIG. 1 suggest the repeated pattern for a healthy subject and its disruption for a subject with sleep disordered breathing (SDB). Arousal threshold increases with increasing stages of non-REM sleep such that it is most difficult to arouse someone from Stage 3 and Stage 4 sleep. The restorative quality of sleep seems to correlate best with the amount of slow wave sleep in a given night. Arousal threshold is variable in REM sleep and may be related to a person's selective attention to internal rather than external stimuli during dream mentation.

Analytical methods and associated visualization can be used to learn and categorize the sleep experience for both healthy and compromised subjects in a manner that permits clear recognition of anomalies in the sleep behavior. This can be used to compare the data for compromised subjects with that of healthy subjects. It can also be useful when the data for an individual is examined over the course of several sleep periods. To express this, characteristic features, "Sleep Signature" and "Sleep Score" are described herein.

The numerous transitions among stages made in a typical night of sleep present "patterns" that may be used as measures of the "quality" of a night's sleep. Over the course of multiple nights, they can reveal baseline behavior for an individual (or a class of individuals) that can be used to classify and better understand sleep disorders. Sleep pattern analysis pre and post intervention can also aid in the qualitative and quantitative assessment of treatment effectiveness.

Figure 1A:
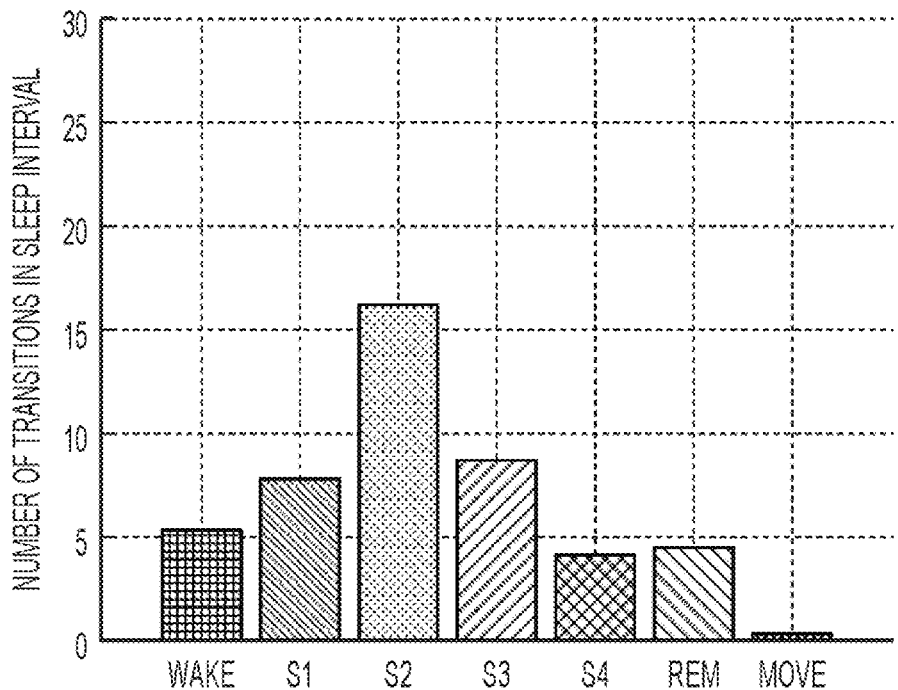
FIGS. 1A and 1B are charts illustrating examples of average counts of sleep stage transitions for different groups of subjects.
Figure 1B:
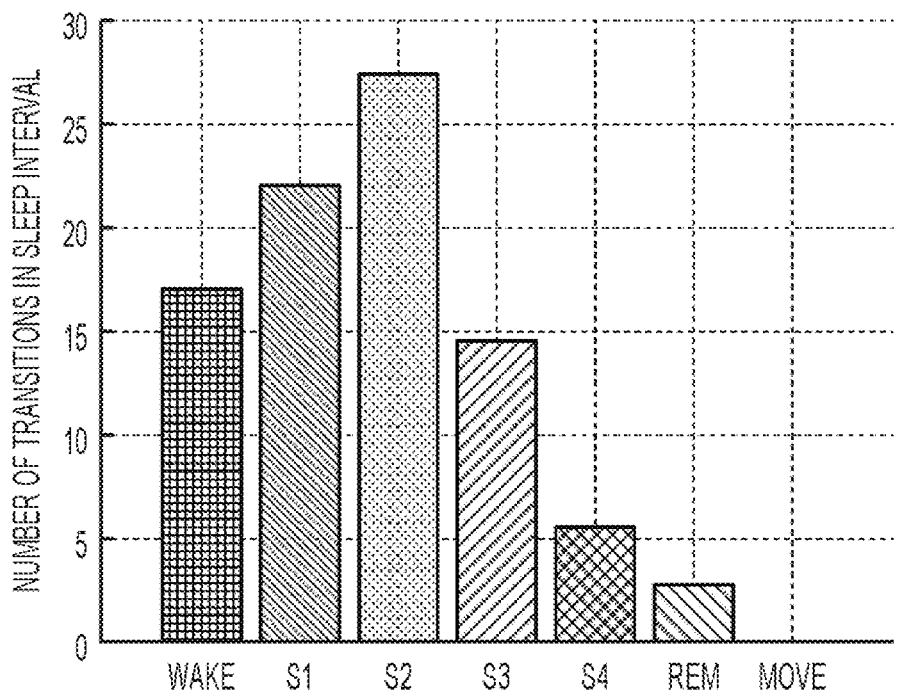

The charts in FIGS. 1A and 1B show the average counts of sleep stage transitions for 16 healthy subjects (left) and 4 subjects with Sleep Disordered Breathing or SDB (right). Plainly the subjects with SDB are more "restless," with many more transitions in the wake and light stages of sleep than the healthy subjects. The numbers of REM and S4 transitions are about the same in both groups; however, the times spent in these "good" stages of sleep are much shorter in the SDB subjects (see FIG. 3 and FIG. 4). A combination of the number of stage transitions and the total or average time spent in each stage can be a useful measure of sleep quality in a night.

Figure 2:
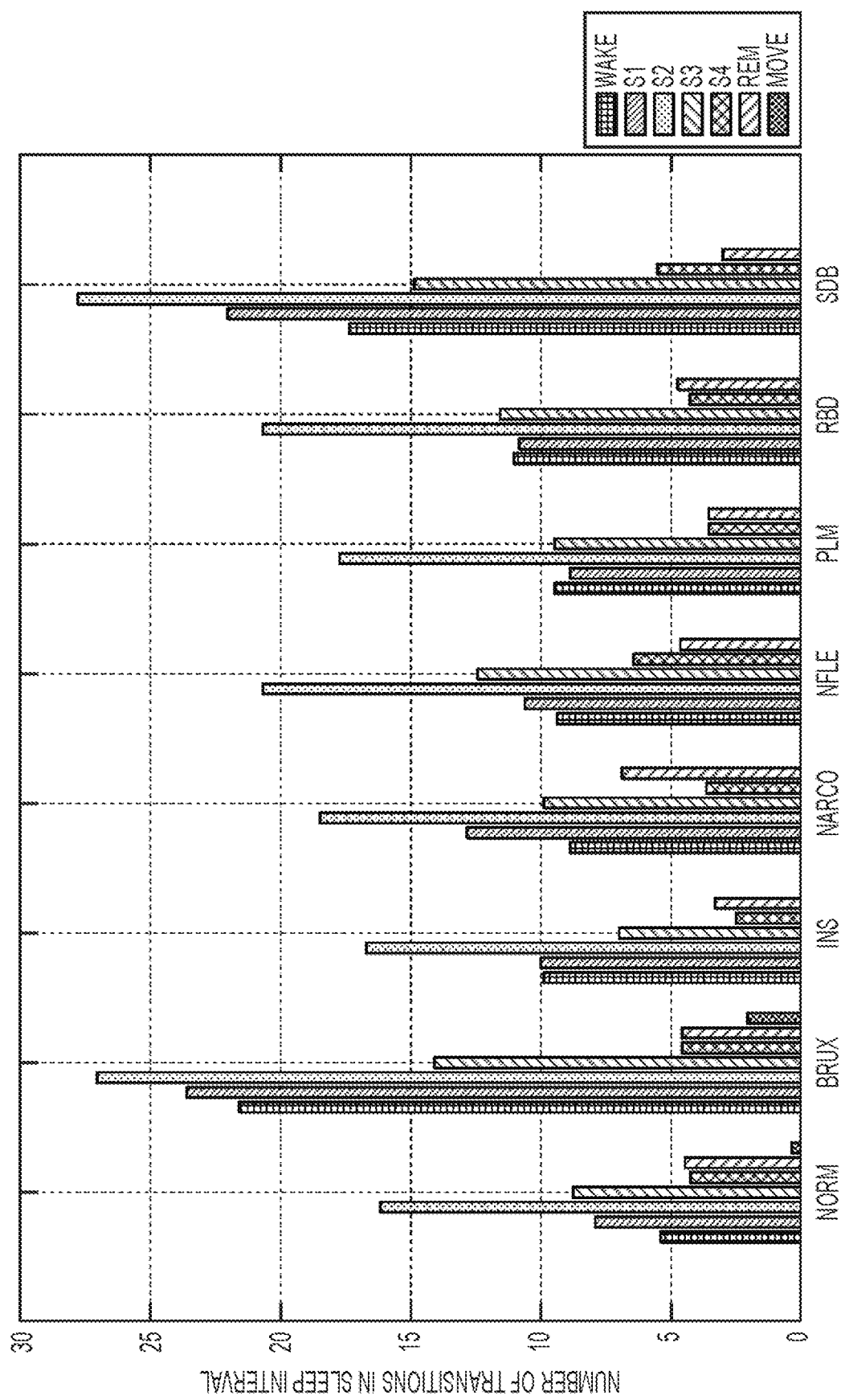
FIG. 2 is a chart illustrating average numbers of sleep stage transitions for groups of healthy and compromised subjects.

FIG. 2 shows the distributions of sleep stage transitions for groups of healthy and compromised subjects with a variety of disorders. In every case the groups of subjects with sleep disorders have much higher numbers of transitions in the wake and light sleep (S1 and S2) stages than do the healthy subjects. The relative transition counts suggest that the ratio of "good sleep" stage transitions (REM and S4) to WAKE transitions can be a suitable discriminator for good and poor sleep between groups. Relative amounts of time spent in each stage can also be accounted for while scoring the sleep quality.

Figure 3:
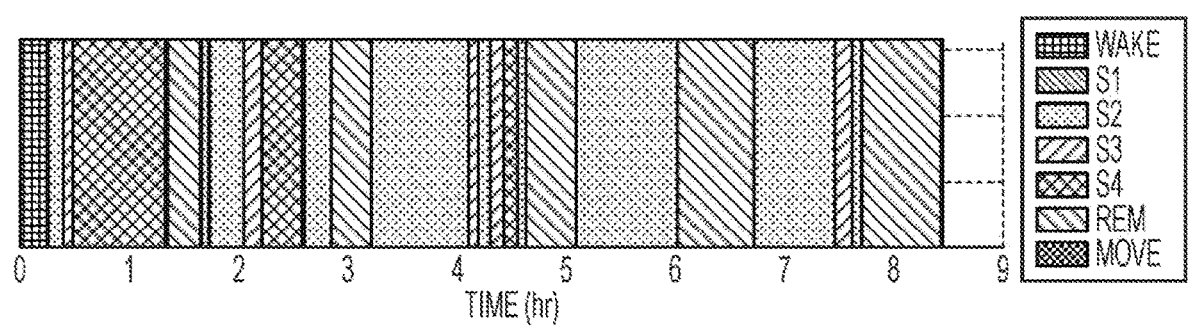
FIG. 3 is a chart illustrating timings and durations of sleep stage transitions for a healthy subject.

FIG. 3 shows the timings and durations of sleep state transitions for a healthy subject (29 year old male with no known pathologies, from the "NORM" group in FIG. 2) having a very good night's sleep. In this example after a period (14.5 min.) of wakefulness the subject passes through 0.5 min of S1, 8 min of S2, 5 min. of S3, 50 min of S4, 1.5 min of S3, 1.5 min of S2, and then 17 min of REM sleep, completing the first of 5 such cycles in the night. The REM stages increase in length as the night goes on. The final REM stage lasts 42 min.

Figure 4:
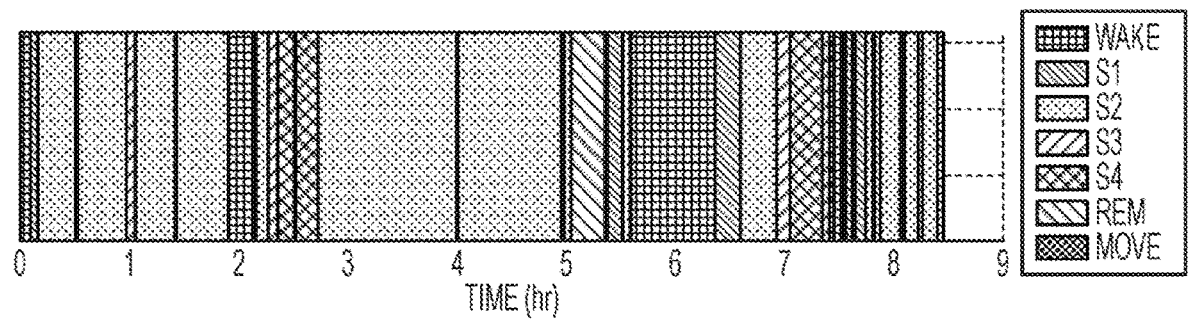
FIG. 4 is a chart illustrating timings and durations of sleep stage transitions for a subject with sleep disordered breathing (SDB).

The data in FIG. 4 are for a subject (79 year old male from the "SDB" group in FIG. 3) with sleep disordered breathing. While the study intervals for this subject and the healthy subject are about the same; the contrasts are quite clear. The SDB subject has only one brief period of REM sleep, scattered intervals of deep (S3 or S4) sleep, and many intermittent periods of wakefulness. The sleep efficiency is lower, and the overall sleep interval is dominated by stage S2, light sleep.

The figures illustrate an intuitive way of displaying sleep stages and events that occur during sleep. Events in this case can be color coded for easy recognition by a user or someone analyzing the data. In this illustrative example Wake is color coded as dark blue, S1 as medium blue, S2 as light blue, S3 as light green, S4 as yellow, and REM as orange. The embodiment shown can also adjust its visualization to the stages being described in less detail such as Wake, light sleep (S1 and S2), deep sleep (S3 and S4) and REM. In some implementations the colors are dark blue for wake, light blue for light sleep, yellow for deep sleep, and orange for REM. The color selection can be made based on the ability of the visualization to draw attention to the stages of highest interest such as REM and slow-wave sleep (deep sleep).

This display can be achieved by taking as input the hypnograms and annotations of the sleep session. This can be in the form of epochs, often 30 s, scored as a particular stage or a list of stages with total durations. Using the time noted or detected by an automated algorithm for filled rectangles are drawn as ribbons with the color of the scored stage and the length of the rectangle corresponding to the duration of the stage. In addition, events such as apnea events can be superimposed on the stages with markers such as a vertical solid line drawn in a specific color per events type to indicate the occurrence of an event at a certain time. Events with a duration to be displayed can be drawn as rectangles in the background with transparencies or with event start and stop markers. This input format allows the method to flexibly plot results of sleep monitoring irrespective of the source. The source, for example, can include hypnograms and annotations scored by a technician from a sleep lab, or automatically scored using the data from the sleep lab, or scored in either way from data obtained from home-tests, wearables and other recording devices. This event display mechanism can be used to display events such as start and stop times of snoring, central or obstructive apneas, hypopneas and other sleep related events.

Figure 5:
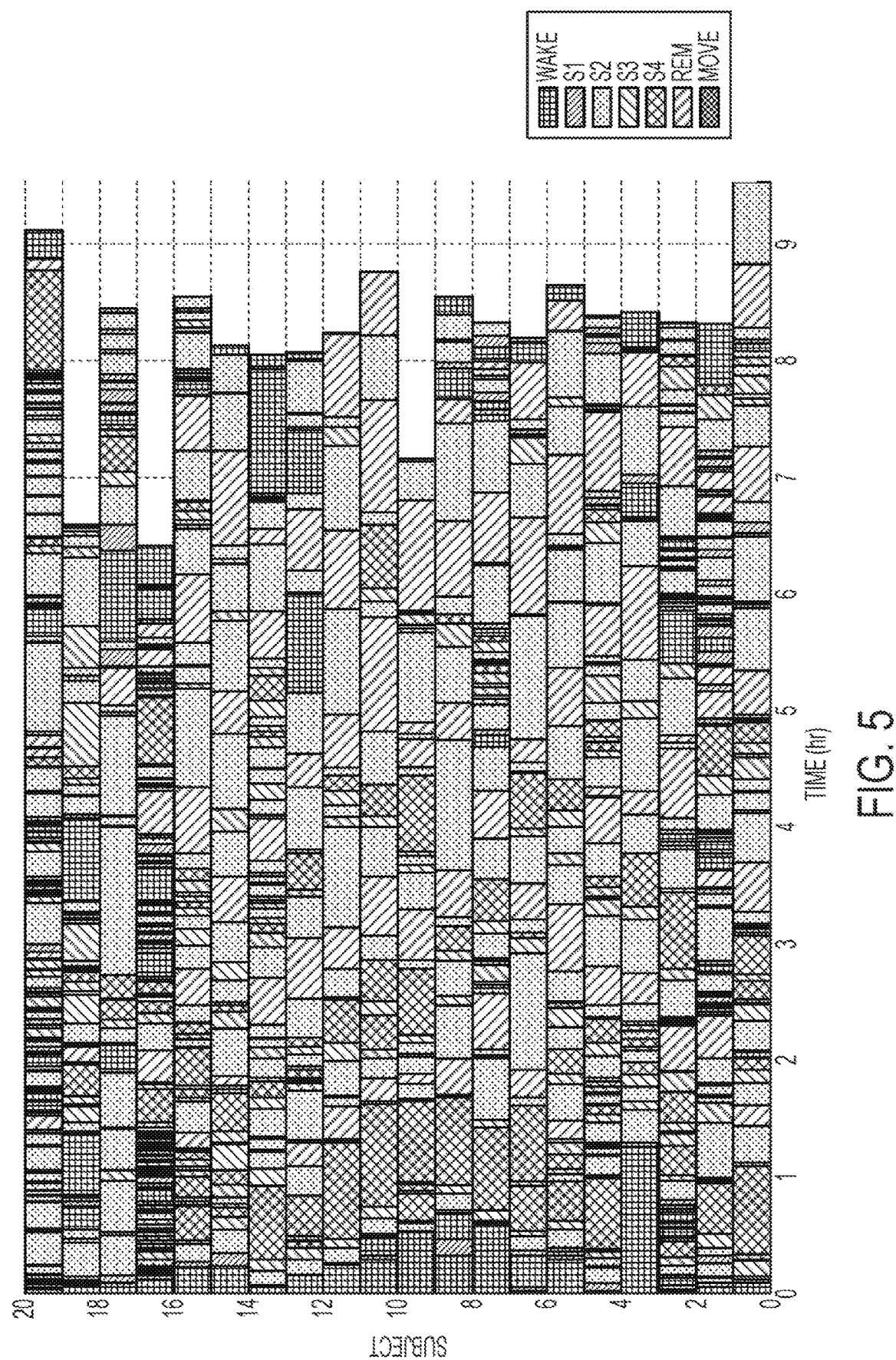
FIG. 5 is a chart illustrating sleep signatures for 16 healthy subjects and 4 subjects with SDB.

FIG. 5 shows a single night of sleep for 20 subjects (from the CAP database). Subjects 1-16 are healthy (the NORM group) and subjects 17-20 have SDB. A pattern can be inferred for the healthy subjects, early entry into deep S4 sleep, and repeated patterns of significant intervals of REM sleep. In contrast the 4 subjects with SDB have much more fragmented sleep and relatively small amounts of REM and S4 sleep.

The visualization method disclosed herein illustrated by these examples is designed to be informative and intuitive while interpreting and analyzing the sleep data recorded over multiple nights. Additionally, it is designed to aid in determination of the "sleep signature" of a group of recorded nights. These nights could be multiple nights for a single subject, for a group of subjects, subjects with a particular common issue, such as a disorder. The signature shown in figures above is plot by relative time, i.e., with the x axis as hours from start. The signature can also be plot by absolute time where the x axis has ticks for hours of the day. In some implementations, naps taken without stages known i.e., without using sleep monitoring but recorded using subjective diaries may also be added to the visualization in a fixed color. These can be added by being appended to the scored hypnograms or added as rectangles starting and ending at the absolute time that they were recorded.

Figure 6:
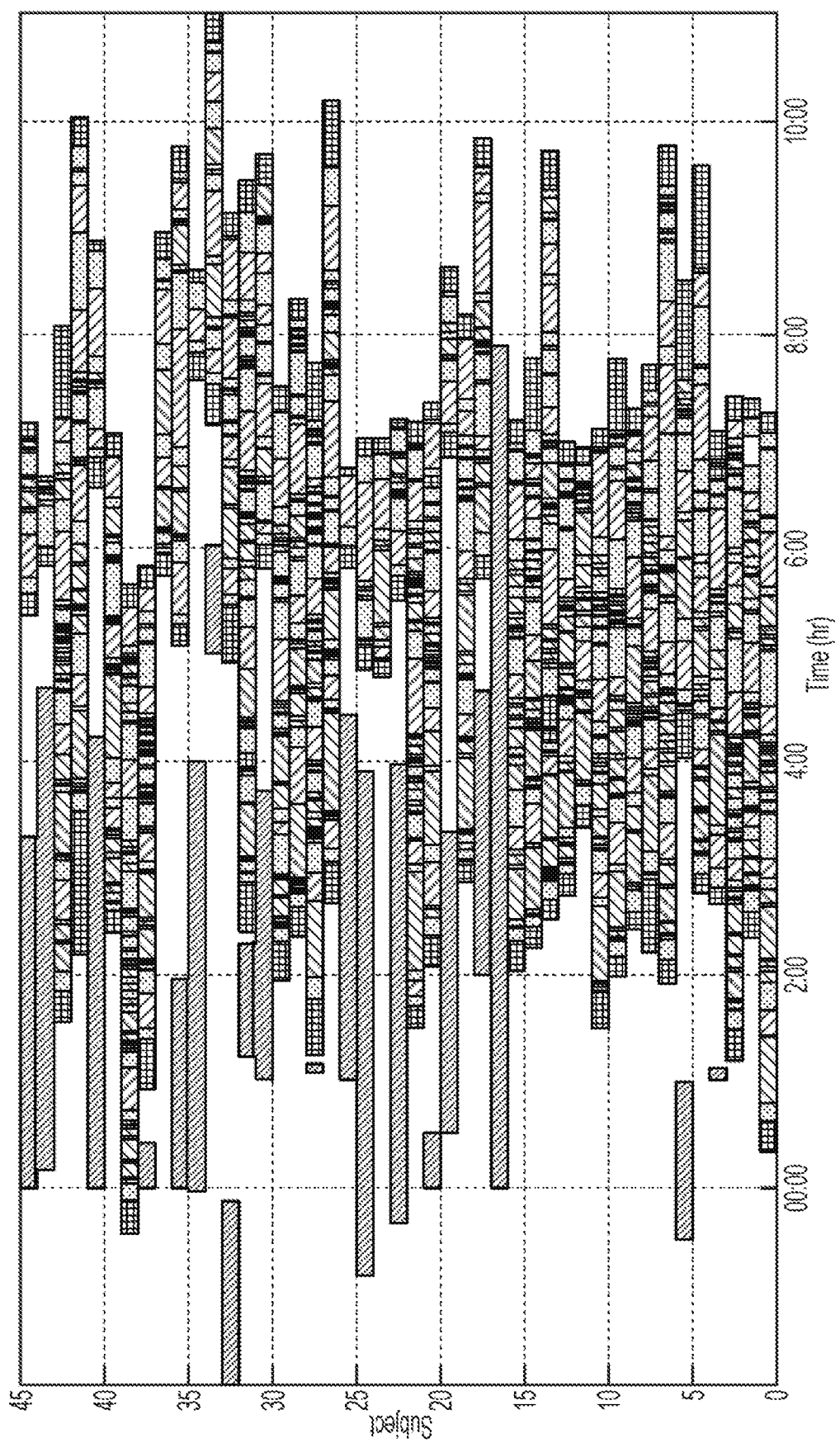
FIG. 6 is an illustration of hypnogram plots in absolute time for a single subject.

FIG. 6 illustrates some implementations that can plot sleep data controlled by a setting in absolute time. Naps can be plotted in a fixed color such as dark green in this illustration. Sleep signatures and architectures can be inferred visually or statistically in absolute time. Several parameters can be included in the sleep signature and architecture description. Sleep Onset Latency (SOL) can be recorded as an average time to fall asleep or a distribution of times to fall sleep, i.e., transition from wake to a sleep stage once the subject lies in bed. Total Sleep Time (TST) can be computed as the total time the subject is in non-wake sleep stages through the night and can be recorded over multiple subjects or multiple sleep sessions using statistical representation such as averages, medians or distributions. These can be recorded as night sleep time, non-night nap sleep time and total sleep time through a (24 hr) period. Similarly, the statistical absolute time the subject sleeps can be recorded as a part of the signature along with the statistical representations of total REM time, total slow-wave sleep time, total light sleep time, total wake after sleep onset, total awakenings. Across multiple sleep sessions the longest REM cycles, longest slow-wave sleep cycles and other similar factors can be aggregated and added to the signature. In some implementations, the relative times i.e., time from lights out time at which each REM cycle starts is aggregated. The same can be computed for slow-wave sleep or deep sleep cycles. Additionally, when the data is represented in absolute time, sleep stage distribution across the 24 hour period can elucidate intrinsic individual circadian and ultradian rhythms. This can be used to determine optimal sleep and wake times as well as to identify circadian rhythm disorders.

This type of analysis can also aid clinicians and patients track their progress during behavioral therapy (Cognitive Behavioral Therapy for Insomnia) intervention often used to treat insomnia. In some implementations, the representation of the absolute sleep signature includes the most probable stage in each 30 minute interval (e.g., 10 pm to 10:30 pm, 2:30 am-3 am etc.), and the probability distribution of sleep stages in each of the intervals. Additionally, the average number of recordings for each type of event, including but not limited to snoring and apnea events, waking up, walking are also recorded as part of the signature. The interval length can be changed programmatically in the embodiment based on the target application. This can be extended to estimate the highest probability sleep stage at any particular time, and the highest probability time of being in a particular sleep stage or sleep event. The visualization and analytics can be used to extract and correlate contributing factors for events such as Sleep Onset REM i.e., REM occurring before slow-wave sleep, and REM rebound i.e., when REM increases in duration especially during early cycles. These often occur after sleep deprivation. These can be correlated to the sleep times and signatures of previous nights and can additionally be correlated to daily habits and events such as coffee intake, exercise, medication which may be logged using a digital diary provided by the system. In some implementations, this diary is in the form of a mobile application.

Longitudinal studies can be important to assess the effectiveness of remediation techniques, including those prescribed or recommended for subjects with disorders such as insomnia, narcolepsy, SDB, etc. and healthy individuals who simply want to sleep better.

To grade a specific session or sleep or discriminate between different sleep sessions a "sleep score" can be computed using the quality and quantities of sleep and sleep characteristics. While sleep is a very complex activity that may not be completely captured in a single figure of merit, a score can nonetheless be useful to users and clinicians alike as a quick method of assessing the effectiveness of measures to improve sleep and tracking progress or the lack of it over longer periods of time.

The sleep score, defined and disclosed herein, is based on an analysis of sleep hypnograms, i.e., the sequence of sleep stages an individual passes through during each sleep session.

The Sleep Scoring method takes as input the hypnogram of a subject's sleep session. While sleep architectures of healthy subjects vary on different nights, by age and other variables, several general trends in the sleep architecture of healthy individuals can be described, modeled, and evaluated mathematically when scoring sleep sessions. These can include observations such as ultradian cycles of sleep stages (approximately 90 minute duration), presence of 4-5 REM cycles, often starting at 15 minutes in duration and then approaching 45 minutes, the duration increasing through the night. Also, slow wave sleep is typically completed in the first half of the night with much lower occurrences in the second half of the night. Additionally, observations in sleep disorders such as very low percent of slow wave sleep (S3 and S4) and in some cases its virtual absence in patients with Sleep Apnea, large Sleep Onset Latencies (SOL) for insomniacs, and larger number of significant awakenings and high Wake After Sleep Onset (WASO)_of subjects with sleep disorders can be weighed in the scoring.

The method employed to compute a sleep score comprises the following steps. The individually scored epochs are grouped together into larger "segments" comprising all continuous epochs of the same stage in cases where a fixed epoch size is scored, 30 s in most sleep labs. Additionally, to account for variations in PSG scorings that can be attributed to the scoring technician's individual preference, or an automated computer method's errors, several less likely progressions, such as two large segments of REM separated by a single 30 second epoch of Wake, can be combined into a single segment.

The method can then compute key sleep parameters such as Sleep Onset Latency, Wake After Sleep, Total Sleep Time, and Number of Awakenings during the sleep session. Sleep Onset Latency can be computed as:

$$\text{Sleep Onset Latency} = t_{SleepOnset} - t_{Lights\ Out}$$

The value $t_{SleepOnset}$ represents a time of first stage which is scored as a "sleep" stage (i.e. S1, S2, S3, S4, or REM). This can alternately be computed as the first epoch which was scored as a sleep stage. In some implementations, the additional condition of at least a threshold duration (e.g., 5 minutes) being continuously also scored as "sleep" is used to detect sleep onset. The value $t_{Lights\ Out}$ represents a time at which the subject first attempts to fall asleep often recorded as the time the lights were turned off in a sleep study.

A Wake After Sleep Onset (WASO) score can be computed as the sum of all segment times scored as "wake" excluding those before the Sleep Onset time and the final wake segment.

A Number Of Awakenings score can be computed as a number of segments scored as wake excluding segments before Sleep Onset and the final wake segment.

A Total Sleep Time can be computed as the duration of the session spent actually sleeping and is computed as the total time in all the segments scored as sleep.

The total cumulative time spent in REM (TotalREMTime) and the total cumulative time spent in Slow Wave Sleep (TotalSWSTime) (S3 or S4) for the night can be computed as the sum of times in segments scored as REM and S3 and S4 respectively. Additionally, the longest REM and SWS segment times (LongestREMTime and LongestSWSTime) are computed, and the total number of segments for each stage can also be computed.

Three key staging sub-scores can be created to capture the most important elements of healthy sleep: REM Score representing the architecture of a subject's REM stages, SWS Score representing the architecture of a subject's deep sleep (identified to be a key problem for patients with disorders such as apnea), and a General Score that can incorporate the overall sleep metrics such as amount of time spent awake vs sleeping.

REM Score can be computed using a combination of total duration of REM through the night and the longest stable REM segment. Each of these factors can be obtained mathematically by weighing the observed time against baseline times for healthy individuals using a combination of logarithmic and Gaussian functions. The REM Score can be further enhanced if it has an increasing length from stage to stage as the night progresses—a trend common in the sleep of the healthiest subjects. The REM Score can be computed by using a scoring function that is defined as:

$$F(c, w, c_w) = \frac{1 - e^{rc}}{1 + e^{rc}} \text{ where}$$

$$r = \frac{\log(1-w)}{\log(1+w)} \Big/ -c_w$$

and where c is the scoring function's value at reference weight, $c_w$

Factors that can be taken into account for REM can be REMTotalDurationScore, a score used to evaluate the total duration of REM (TotalREMTime) achieved in the night, and REMLongestSegmentScore, which evaluates the longest REM period in the night.

In some implementations REMTotalDurationScore is a function of TotalREMTime and defined as REMTotalDurationScore=$F$(TotalREMTime,0.5,40)

and REMLongestSegmentScore is defined as

REMLongestSegmentScore=$F$(LongestREMTime, 0.5,20)

In some implementations the REMScore increases if the REM stages demonstrate an increase in length through the night, a phenomenon present in the healthy subjects. A REMAcendingFactor can be computed by computing the difference in successive stages and expressed as a percent of these differences that is positive. An initial REMScore can be computed as a weighted mean of REMTotalDuration-Score and REMLongestSegmentScore with weights of 0.7 and 0.3 respectively in some implementations. Further, if the REMAscendingFactor is greater than a threshold, 0.7 in some implementations, the final REMScore is defined as $$REMScore = \frac{\sum_{i=1}^{n} x_i w_i}{\sum_{i=1}^{n} w_i}$$

The initial REMScore can be adjusted based on the REMAscendingFactor:

$$REMScore = REMScore^{0.5 + \frac{1 - REMAscendingFactor}{2}}$$

Similarly, the SWS Score is created using the total and longest SWS stage times and further weighted based on the amount of SWS sleep being completed within the first 4 hours after Sleep Onset—a trend common in the sleep of the healthiest subjects.

In some implementations SWSTotalDurationScore is a function of TotalSWSTime and defined as SWSTotalDurationScore=$F$(TotalSWSTime,0.5,40)

where TotalSWSTime is the sum of sleep times spend in S3 and S4 stages. This takes care of both the AASM and R&K standards of sleep scoring.

The parameter SWSLongestSegmentScore is defined as

SWSLongestSegmentScore=$F$(LongestSWSTime,0.5, 20)

and LongestSWSTime is the longest sequence of the subject being in either S3 and/or S4 stages.

In some implementations the SWSScore increases if a certain amount of SWS sleep is achieved in the first four hours of the night, a phenomenon present in the healthy subjects. An SWSHalfNightFactor can be computed as SWSHalfNightFactor=$F$(SWSHalfNightTime,0.5,40)

An initial SWSScore is computed as a weighted mean of SWSTotalDurationScore and SWSLongestSegmentScore with weights of 0.8 and 0.2 respectively. Further, if the SWSHalfNightFactor is greater than a threshold, 0.7 in some implementations, the final SWSScore is defined as $$SWSScore_{Final} = SWSScore^{0.5 + \frac{1 - SWSHalfNightFactor}{2}}$$

The GeneralScore can be computed as a geometric mean of two separate scores created to evaluate Wake After Sleep Onset and Total Sleep Time. The Wake After Sleep Onset Score (WASOScore) can be a number that decays in a gaussian trend as the time awake after sleep onset increases, and Total Sleep Time score (TSTScore) can compare the proximity of the Total Sleep Time to the recommended 7-8 hours of sleep.

$$WasoScore = g(x, \mu_{waso}, \sigma_{waso}) \text{ where}$$

$$y(x, \mu, \sigma) = e^{-0.5 \times \frac{((x-\mu)/\sigma)^2}{\sqrt{2 \times \pi} \times \sigma}} \text{ and}$$

$$g(x, \mu, \sigma) = \frac{y(x, \mu, \sigma)}{y(\mu, \mu, \sigma)}$$

In some implementations $\mu_{waso}$ is set at 0 and $\sigma_{waso}$ at 40 minutes.

TSTScore can be assigned by a function that is set to [1 0.8 0.6 0.4 0.2 0] at reference values of [7 5.5 4 3 2 1 0] hours of sleep and interpolated for a TotalSleepTime of x hours linearly in between the two reference values that form a range that contains "x".

The GeneralScore can be defined as a geometric mean of WASOScore and TSTScore.

$$\bar{x} = \left( \sum_{i=1}^{n} x_i^{w_i} \right)^{1/\sum_{i=1}^{n} w_i}$$

In some implementations these weights are defined as 3 and 1 respectively.

The SleepScore can be computed as a weighted mean of the REMScore, SWSScore and GeneralScore. In some implementations this is computed with weights of 0.4, 0.4 and 0.2 respectively. Additionally, a light sleep score is computed to evaluate the S2 stages in sleep, as a fractional representation of being 50%

The parameters and weights used to arrive at the final sleep score can be tuned using statistics across databases of sleep sessions and tuned to reflect patients outcomes such as sleep satisfaction reported by the subjects. These patient outcomes can also include performance tests which may be monitored over multiple days. Determination of weights can be achieved using neural nets trained over a large number sleep sessions for the desired turning output.

Figure 7:
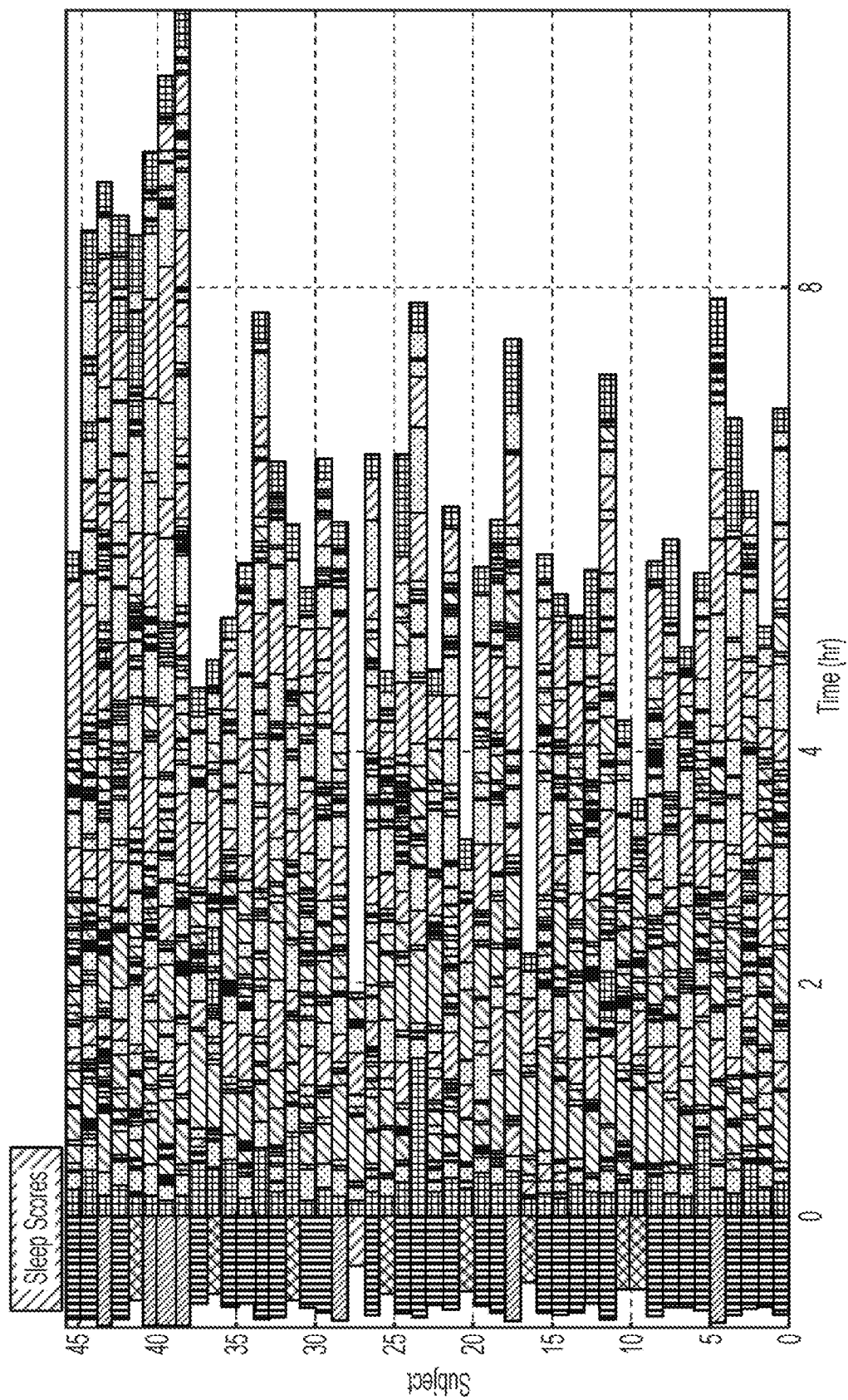
FIG. 7 is a chart showing hypnograms for 45 nights of sleep for a single subject with scores plot as bars on the left.
Figure 8:
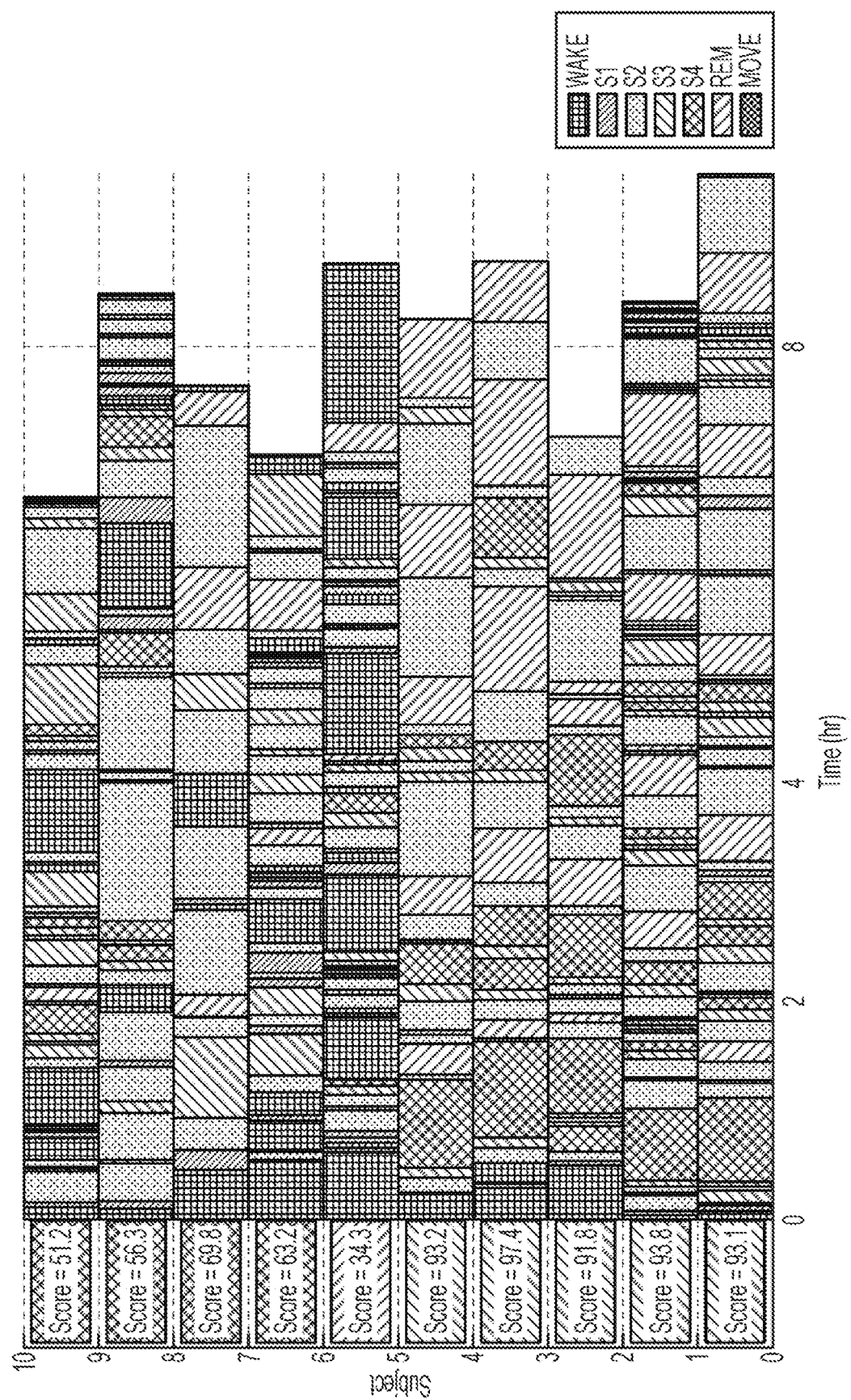
FIG. 8 is a chart showing hypnograms for healthy subjects vs. subjects with sleep disorders, as well as corresponding sleep scores.

FIG. 7 is a chart showing hypnograms for 45 nights of sleep for a single subject with scores plotted as bars on the left of the hypnograms. FIG. 8 is a chart showing hypnograms for healthy subjects vs. subjects with sleep disorders, as well as corresponding sleep scores. The sleep architectures of the compromised subjects in FIG. 8 are marked with long Wake periods (dark color), large numbers of awakenings, and severe reduction SWS sleep resulting in lower Sleep Scores (highlighted in on the left side), and some "poor" sleep scores (e.g., ranging between 30 and 70, compared to scores of 90 and higher for other subjects.

In some implementations, these scoring parameters can be made more pertinent to daytime performance by tuning them to optimize a cost function that incorporates corresponding evaluations of patient outcome. These outcomes may include sleep satisfaction questions, self-evaluations of well-being, physical and cognitive ability.

Further, a log describing the daily habits of the subject during the day can be maintained. These can include details such as exercise, walks, exposure to sunlight, medication, naps, and travel. In addition, subjective evaluations of feeling such as well-being, stress, fatigue, tiredness, alertness, fun, happiness, healthiness, success can be maintained to track these parameters individually and find correlations in sleep patterns, and metrics with these variables. The correlations for these large datasets can be found using neural nets implementing deep learning. Multiple sleep metrics such as REM time, score, transitions, longest rem, slow-wave sleep time, score, longest slow wave sleep, sleep onset time, absolute times of different sleep events, and daily habits and their evaluations can be trained in the neural net to map them with weights to sleep and health outcomes that are logged in the diary. These mechanisms can be used to find the factor or factors that may be leading to the poor sleep quality or the improved sleep quality. Trends over multiple days (e.g., 3 days) can also be used to track sleep debts and their effects. The model of sleep and sleep debt can be determined with respect to performance and self-evaluations using deep learning for the sleep parameters and variables, quantitative and subjective, disclosed herein.

In some implementations, these features are provided to the user in a mobile application. The mobile application allows the user to input their sleep evaluation as a questionnaire. The user can input sleep times, awakenings, sleep onset time and other sleep details, sleep satisfaction such as tiredness, feeling of being rested, alertness, irritability etc. Daily habits of travel, caffeine, medication with dosage, exercise, pain and fatigue can also be entered into the application in an easy and intuitive way. Moods such as irritability, happiness, fun etc. can be entered using questionnaires and images or emoticons that represent it and make it easy to select for the user. The date and time for each of these entries can be logged by the system. The recorded date and time can be used to determine if the entry is for the current day or for previous day. This difference can be used to weigh the accuracy and reliability of diary entries to account for cases where entries for a day in the past are being made at a future date. These type of entries can be considered to be less reliable.

The mobile application can provide interactive reaction time tests to the user with the mobile application. In some implementations, the user is prompted to tap the screen when each of 10 balls falls vertically from the top of screen. The user is penalized for preemptive taps and then a score is computed using a weighted mean of the different attempts. In some implementations, the user is penalized for preemptive taps but the score is not weighted equally with the best and worst times being weighed the least. In another embodiment the reaction time and performance is tested by the user's ability to read scrolling text, answer questions later related to the text and tap the screen when a particular color is displayed in the text. This can test the user for memory, reaction time and alertness. The user can be prompted to attempt the test multiple times a day with a graphical display showing the progress over the day and over longer periods of time spanning multiple days. In some implementations, diary entries such as sleep satisfaction, mood and well-being, habits, and reaction time tests can be graded and combined into a Subjective Sleep Score. This can be achieved using parametric fusion techniques and weights as disclosed herein for the Sleep Score computation. Alternately, multiple questions and parameters such as the reaction time test score can all be given grades on a scale. The individual grades for each contributing question or parameter can be used to compute a weighted mean. This result can be normalized to the desired range and presented and recorded as a Subjective Sleep Score. In some implementations the Subjective Sleep Score and Sleep Score as fused using a weighted mean into an Overall Sleep Score.

In some implementations where the invention is presented to the user as a mobile application, the application can be configured to send the user personalized reminders and alerts. These alerts can be user defined such as an alert that it is time to get ready for bed, or time to cut off caffeine intake. The reminders and alerts can also be automatically generated by the computer system based on trends in sleep quality and quantity. As an example the mobile application may detect that a subject has sleep issues when they work out after a certain time in the evening and send them a reminder not to do so around that time. The time that a reminder or recommendation is delivered to the subject can also be determined by the method. Times and situations, in which subjects are most likely to take and incorporate suggestions and recommendations, can be experimentally determined. These can be further refined with expected behaviors, such as the possibility of subjects disregarding sleep hygiene recommendations when they are performing, or feeling, their best.

As an example, subjects perform certain tasks well, possibly better than usual, after being sleep deprived for a night. This increased performance can possibly be attributed to adrenalin and this day could be deemed as less effective for behavioral change recommendations. However, if the sleep deprivation continues this could lead to decreased performance as the sleep debt accumulates. This time of decreased performance can be considered to be a more effective time for a sleep behavior change recommendation as the subject is experiencing lower performance and possibly experiencing physical fatigue. The method, in some implementations, determines personalized sleep hygiene and sleep improvement recommendations for the subject. In some implementations, the recommendations are delivered to the subject at times that the method automatically determines to be times that the subject is more likely to act on suggestions. In some implementations, the mobile application tracks if there is a gap in the subject's usage of the diary or the system. If there is a gap in usage the system can ask the subject if it is due to better than average sleep and experiences or due to bad stretches. Often subjects are less likely to enter diary entries when things are going very well or very bad. The response can be taken into account into the long-term sleep assessment.

In some implementations, where the mobile application is integrated with a system that receives sensor data and uses automated methods to determine sleep staging, the sleep metrics and staging data is graphically shown to users and clinicians in a format similar to sleep signature displays shown above. In some implementations, after entering sleep questionnaires, the user can view their objective sleep data as a visualization. The sleep stages are shown on the screen with a circle above that contains the "sleep score" that is computed. The score circle also comprises four quadrants that are dedicated to REM, slow wave sleep (Deep sleep), Wakefulness, and Light sleep aspects of sleeping. Using the REM score, SWS score, General Score, and Light Sleep Score, the quadrants are shaded from the center to the exterior up to the fraction of the respective score. In other words, in some implementations if the REM score is 0.75, the REM quadrant is shaded orange up to 75% of the exterior outline. The total times of each stage are also written on the screen for the user, and a zoom in view of multiple nights revealing the sleep signature is provided in some implementations.

FIGS. 9-12 are screenshots from a mobile application embodiment of the invention. The mobile application may provide, e.g., login screens, dashboards, reaction time tests and results, diaries, habit entries, interactive user screens, acknowledgement screens, and multiple night sleep stage graphs, and displays of sleep score and stage scores, overall times and quality.

Figure 9:
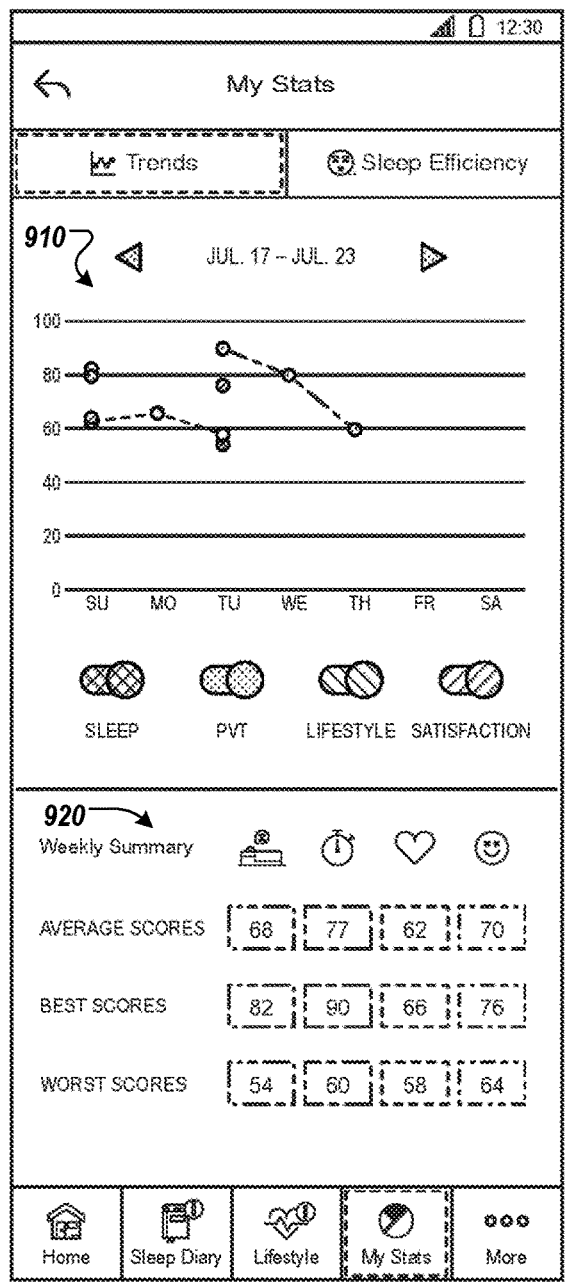
FIGS. 9 and 10 are diagrams that illustrate user interfaces of a mobile application showing scores and graphs of sleep measures of a subject.
Figure 10:
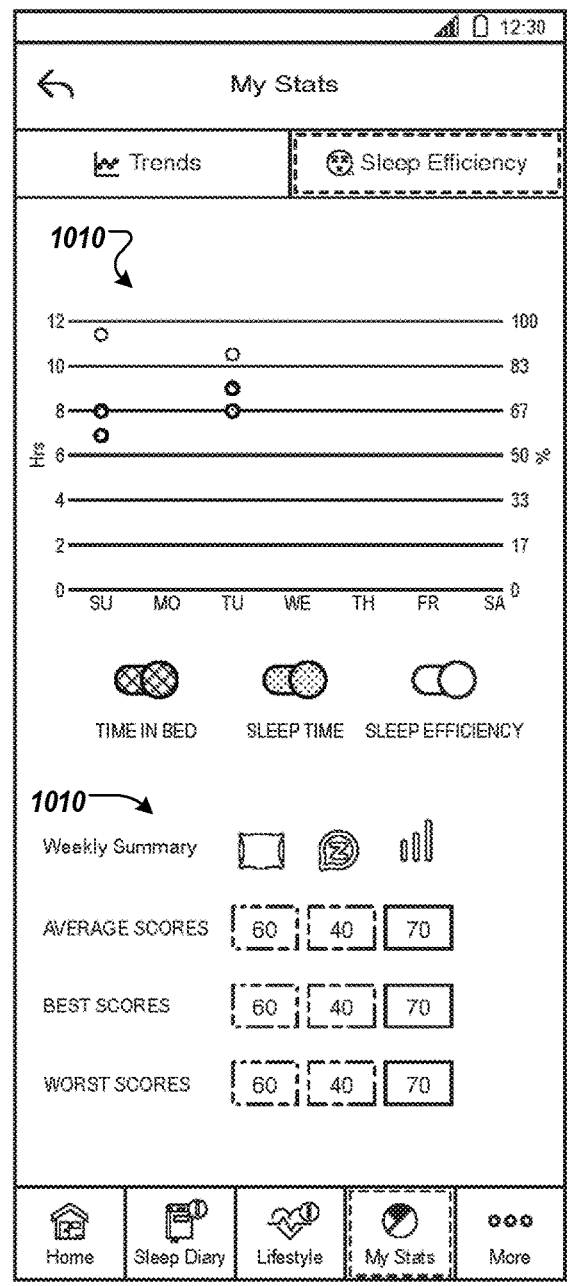

FIGS. 9 and 10 illustrate a "my stats" view of the mobile application. FIG. 9 shows trends in the user's sleep. For example the user interface shows information about a one-week period and sleep sessions that occurred during that period. The user interface shows a line graph 910 of various measures for the user. For example the graph can show measures of sleep quantity, quality, or a sleep score as discussed above. The chart can also show trends in measures of other factors, such as lifestyle elements or reported sleep satisfaction. The lower section 920 of the user interface shows a weekly summary with average scores, best scores, and worst scores for various dimensions of the users sleep and well-being. The scores can be provided for a number of different aspects, such as total amount of sleep, quality of sleep, reaction time, sleep satisfaction or mood, and others.

FIG. 10 is a view of the user interface of the application showing measures of sleep efficiency. For example, the user interface shows a chart 1010 showing amount in of time in bed versus amount of time sleeping during the time in bed. From these measures, a sleep efficiency score can be generated. The sleep efficiency score can be displayed in the chart also. The lower portion 1020 of the user interface shows a weekly summary with average scores, best scores, and worst scores for multiple aspects of the users sleep. For example the scores may be provided for the time in bed, the time sleeping, and sleep efficiency. The information on these charts and in this course helps the user to understand patterns in his sleep across multiple sleep sessions, e.g., sleep during different nights.

FIG. 11 shows a user interface of the application having multiple hypnograms numbered 1 through 7, each corresponding to a different night. The hypnograms are aligned with a common horizontal axis that represents time. The arrangement of the hypnograms distributed vertically as shown, allows the user to quickly understand the total duration of each sleep session by the overall width of the hypnogram, the sleep architecture of each sleep session in the distinct segments corresponding to sleep stages, the relationship of each sleep session with respect to the time of day due to the horizontal alignment, as well as other factors. This display technique efficiently uses the limited screen space of the user's mobile device, such as a mobile phone.

FIG. 12 shows additional detailed information for a single sleep session, e.g., a single night of sleep. The circular chart 1210 at the top of the user interface shows an overall sleep score of 93 for the sleep session. Other scores are indicated in the four quadrants of the circular chart. The size or blanks of these segments represents the value of the score for different aspect of sleep. For example one segment represents a RAM score, another represents a slow wave sleep score, another may represent a transition score indicating how many transitions occurred during the sleep session between sleep stages, and another may represent a duration of sleep. Other scores may be indicated in a similar manner. Below the circular chart, the overall sleep duration of eight hours and 11 minutes is indicated. Of this overall sleep duration, the user interface indicates the amount of time spent in each of multiple different sleep stages. For example the interface indicates that the user was awake for 29 minutes of the sleep session, the user was in light sleep for four hours and 13 minutes of the sleep session, the user was in deep sleep for one hour and 45 minutes of sleep session, and the user was in the REM sleep stage for two hours and 12 minutes of the sleep session.

At the bottom of the user interface a hypnogram for the sleep session is shown. Hose information indicating positions of the user's body at different times is also shown. This information can be shown in alignment with the hypnogram, so the viewer can determine the pose of the user's body at particular times and sleep stages indicated by the hypnogram.

While the illustrations above are customized for a user, the information detected can be presented in a clinical report to be interpreted by a clinician such as a sleep specialist, behavioral psychologist or a primary care physician. The test on which the report is delivered can be a single night sleep study or a multiple night sleep study such as 1 week or 2 week or more. This report can have a high level text summary outlining the findings of the sleep study such as mild apnea, heavy snoring, deficient slow-wave sleep, unremarkable REM cycles. This can be followed by each sleep parameter and metric evaluated such as sleep onset time, REM time etc. shown in the range (min and max) for healthy subjects of the same age group as the subject. The entry can be highlighted in some color such as red or bolded if it is not within the normal bounds much like a lab blood test. The next section can contain the individual nights with graphical representation and then the sleep signature for multiple nights with sleep metrics aggregated over multiple nights and compared to norms. In some implementations which includes methods to correlate poor sleep with habits and subjective evaluations, the possible triggers and reasons for poor sleep can be highlighted in the report. An example of this can be "irregular sleep times", "late physical exercise" or "late caffeine intake." The method is designed to distinguish that some subjects, for example, may be able to drink caffeine late and go to sleep well, whereas it is the primary reason for poor sleep in someone else.

When prescribed to do so, the application and the subsequent report can be used for adherence tracking, i.e. evaluating a subject's adherence to the clinician's recommendations. This can be used to detect and report details such as going to sleep at the same time, sleeping in a cold room at 65 degrees etc. The adherence to different recommendations can be made part of the clinician report.

Figure 13A:
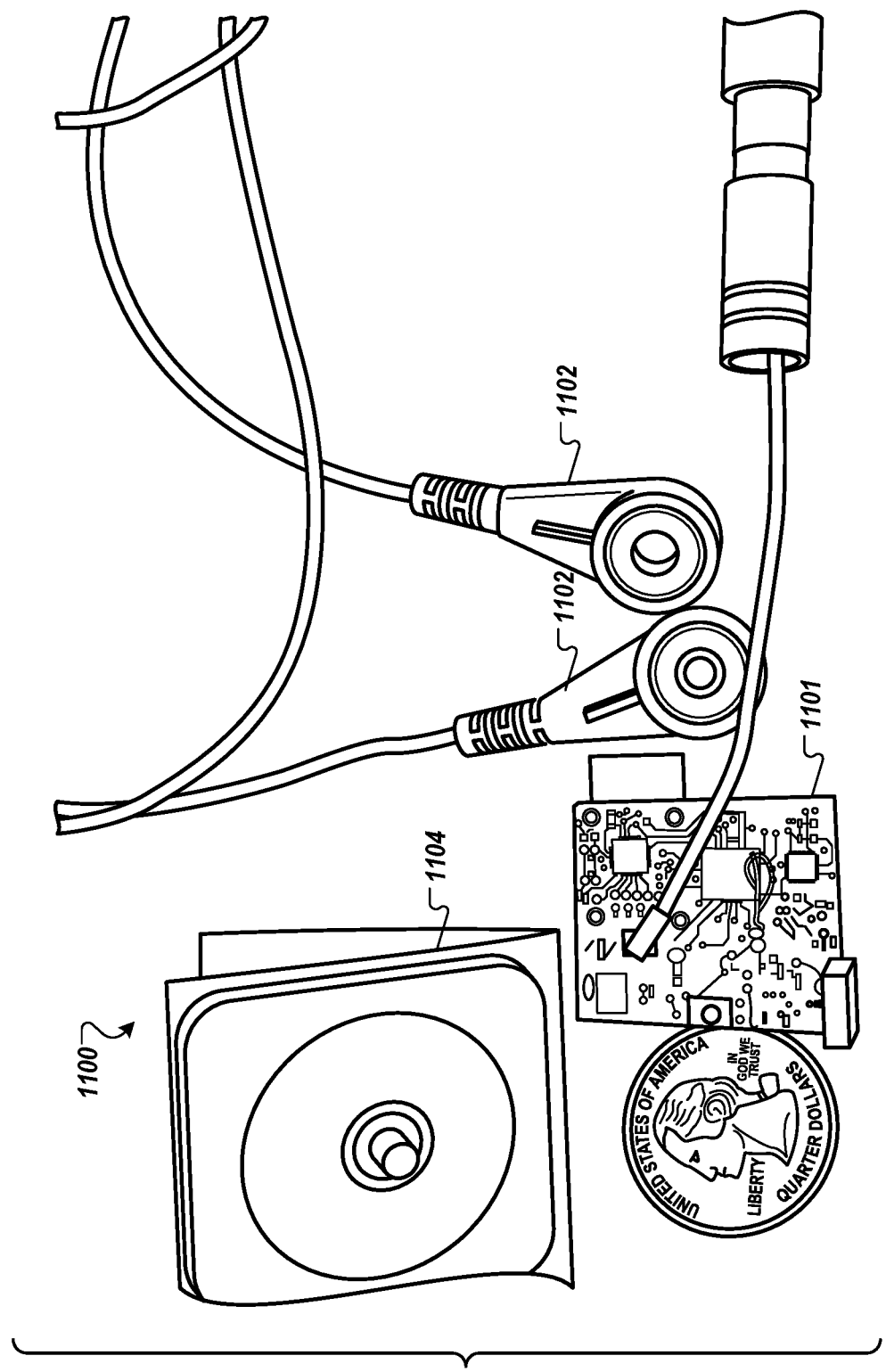
FIGS. 13A and 13B are illustrations of an example of a wearable body data recorder.
Figure 13B:
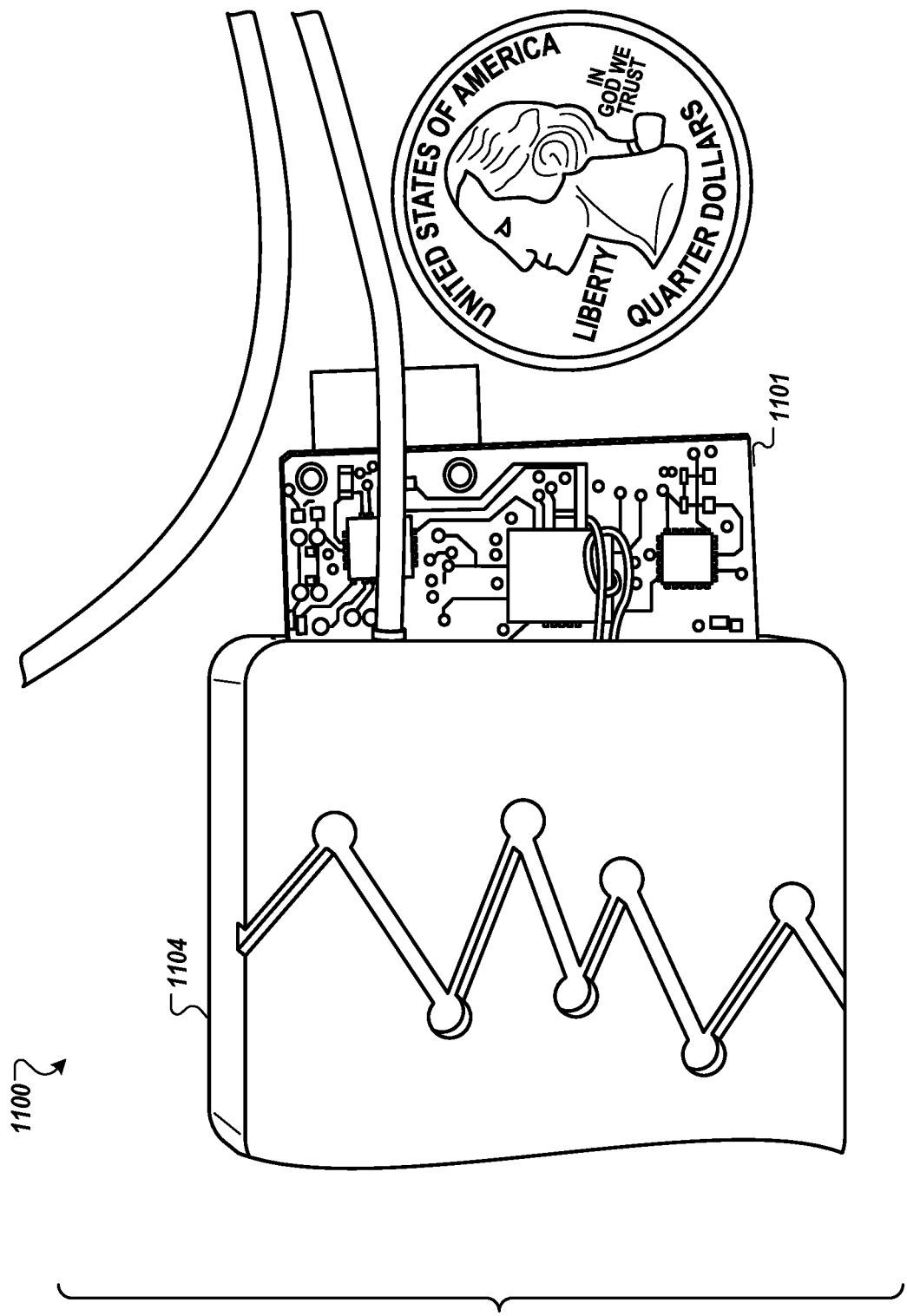

Referring to FIGS. 13A and 13B, the source of the hypnograms visualized, or the sensor data used to generate hypnograms can be a wearable device coupled with staging and event detection analytical methods. In some implementations, the source of the data is a miniature wearable device 1100, referred to herein as a Body Data Recorder (BDR). The BDR has been reduced to practice as a dual-sided 4-layer circuit board designed to achieve a miniature form factor (~1 inch$^2$) housing 3-axis accelerometers, 3-axis gyroscopes, microphones, heart rate sensors, temperature, and light sensors, among others. An image of a U.S. quarter dollar coin is included in FIGS. 11A and 11B as a visual size reference showing the scale of the device 1100.

In some implementations, the combination of sensors has been selected since the data provided can be used for detection of sleep staging with acceptable scoring accuracy, and for recording ambient signals of light and sound to assess the suitability of the environment and in tracking adherence to clinician recommendations. The device also supports detecting and quantifying apnea events and snoring using a built-in microphone. Specifically, the above features can be achieved and provided in a small form factor at an affordable price. The small form factor allows the device to be worn in a location such as the chest all night or day for multiple nights without causing discomfort. This can be critical to the target application.

The body data recorder has been designed to be small, low power, and to fit comfortably in clothing, where the contacts can even be provided using conductive polymer. The parts selected and populated on the dual-sided board for some implementations include the following specific components, though alternatives will be apparent to those skilled in the art: an AD8232 providing single lead heart rate monitoring and serves as an integrated conditioning block for ECG and instrumentation amplification sampling up to 2 kHz, Invensense 6 degree of freedom Inertial Measurement Unit (MPU6500), Knowles MEMS omni-directional microphone with 100 Hz~10 kHz and −18 dB±3 dB sensitivity, TEMT-6000 high photo sensitivity ambient light sensor from Vishay Electronics, TMP102 temperature sensor from Texas Instruments, U.FL connector for delocalization of sensor pads via a miniature RF connector for high-frequency signals up to 6 GHz manufactured by Hirose Electric Group, Communications: microSD, low power blue-tooth (BLE) from Microchip, 1000 mah Li polymer battery, sensor cables, and sensor pads (3M) and 3-D Printed prototype packaging. A circuit board 1101 on which data storage, sensors, processing devices, etc. are mounted can be places in a protective housing 1104.

In another embodiment, the device can support both 3-lead and 2-lead EKG sensor pads, where the left thigh is where the 3rd EKG lead is connected for higher EKG amplitude. In this embodiment, the device is equipped with Wi-Fi to communicate with routers, mobile phones to transfer data. Wi-Fi can be used in this embodiment to upload sensor or processed data to servers for storage or to execute further processing to achieve goals such as stage classification or apnea event detection. In this embodiment the light sensor is a TAOS TFL2561 FN, and the microphone an Invensense INMP401. A digital signal processor from Microchip is used to ensure high sampling rate logging to the microSD card of all sensors, long device life and upload and transfer via Wi-Fi. An ESP8266 Wi-Fi module is used for the Wi-Fi communications. In one implementation, the sensor pads on the body are connected to the board using sensor cables. In another implementation, the two sensor pads for the two-lead version snap into button connectors built into the device packaging. The inside of these snap connectors are wired to the board to establish the connection. In one implementation, disposable sensor pads can be used, replacing sensor pads every time the device is used for a new session.

Any appropriate off-the-shelf motion sensor with even a single axis accelerometer can be used to enable the methods disclosed herein, along with light and microphones with varying sensitivities, when available. Any EKG source or derived heart rate sensor or pulse-rate monitor such as wearable watches can be used by the methods disclosed herein to analyze sleep events and detect sleep staging.

The two EKG sensor pads are worn on the pectoral muscles (i.e., on the rib cage—left and right). This location has been selected after experimentation to reduce muscle activation artifacts in the EKG signal. In some implementations, these sensor pads are provided via conductive polymer that can be built into a t-shirt or garment, e.g., a flexible fabric item of clothing.

A comprehensive sleep monitoring and analytics system can include a wearable device that records sleep data, a mechanism for the subject to enter data, a communications link for data and entries to be transferred to a computer system, an additional system that converts the data into sleep results, such as sleep stages and events, and a mechanism to generate clinical reports from the data and results.

Figure 14:
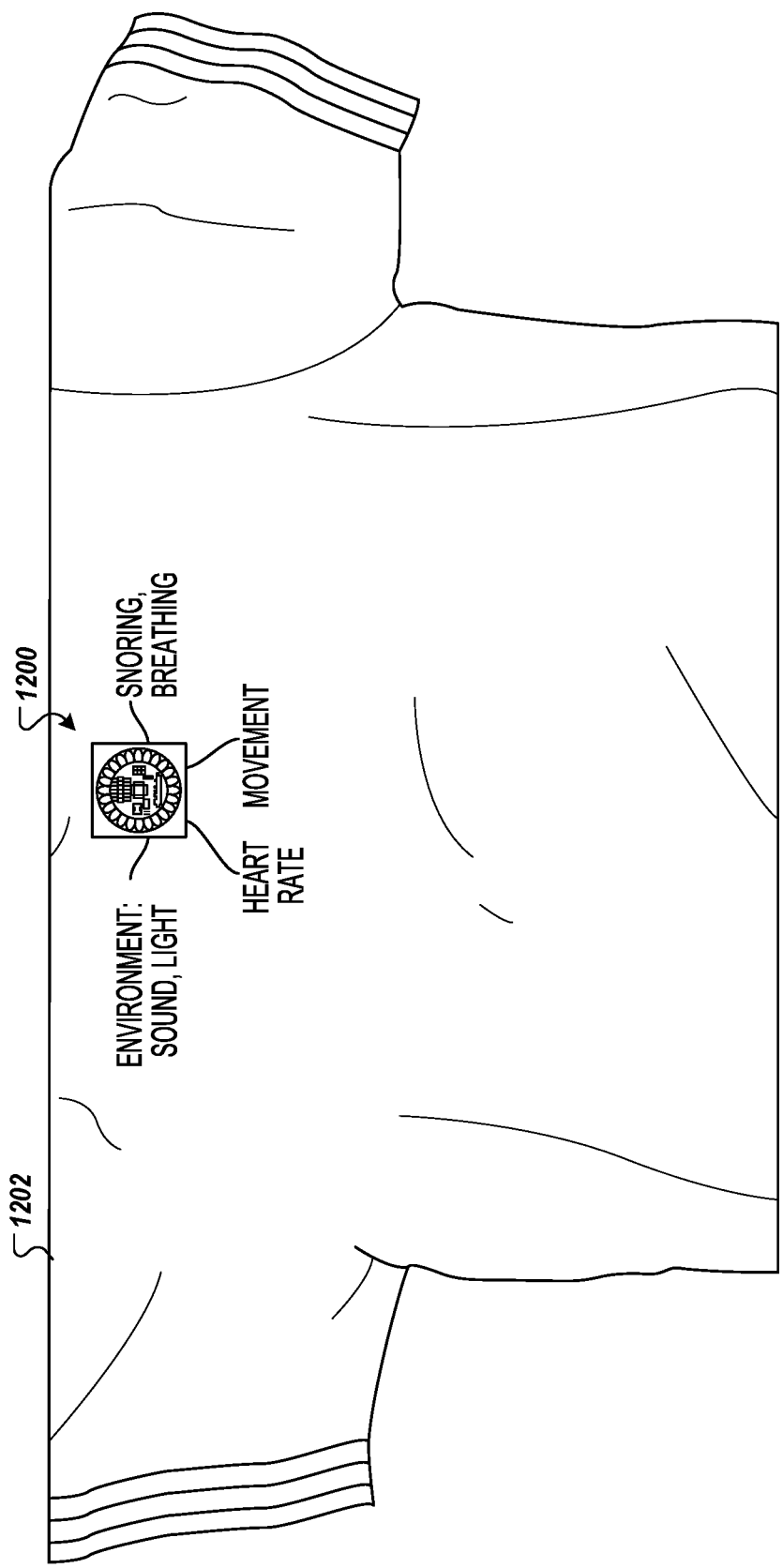
FIG. 14 is an illustration of an example of a T-shirt housing wearable sensors, for use with a body data recorder.

Referring to FIG. 14, in some implementations, a body data recorder 1200 may include a t-shirt 1202 or other garment that houses multiple sensors. The t-shirt can be worn by the subject during sleep sessions, or even all day if the subject chooses.

Figure 15:
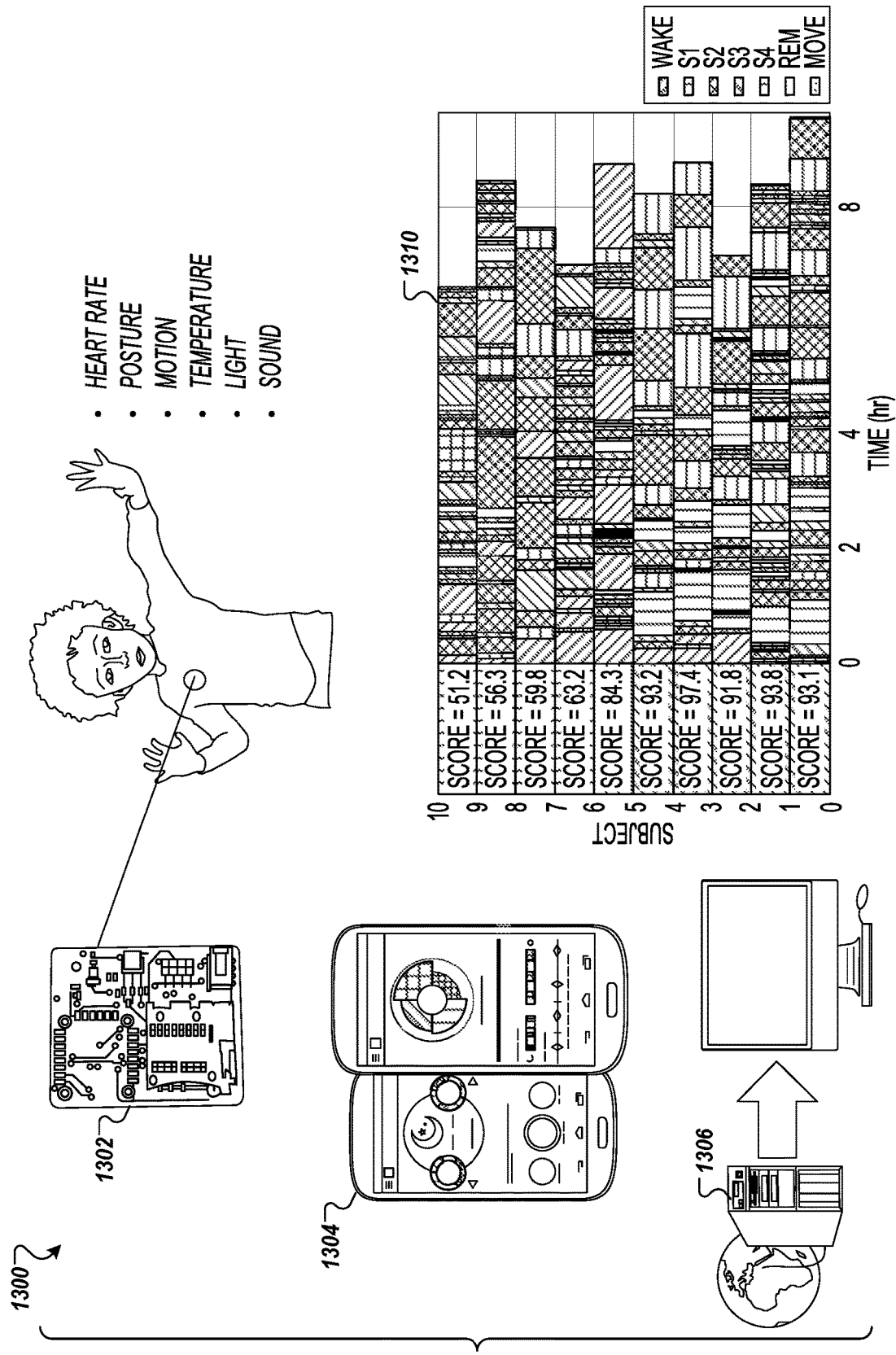
FIG. 15 is a conceptual drawing illustrating example of the components of a sleep monitoring system.

Referring to FIG. 15, a system 1300 for measuring sleep information, performing sleep staging, and generating visual representations and scores can include a BDR 1302 with multiple sensors, a mobile device 1304 that communicates with the BDR 1302, and a server 1306. The data from multiple sensors of the BDR 1302 is recorded and can be transferred to a mobile application of the mobile device 1304 via a link such as Bluetooth or low energy Bluetooth. The mobile application also enables the subject to make the diary entries of sleep times, moods, habits, and sleep satisfaction questionnaires. The mobile application also enables the subject to take reaction time tests.

The mobile application can upload the data to the server 1306 over a link such as Wi-Fi or cell links. Alternately, the data can be transferred from the device or the mobile app via Bluetooth or Wi-Fi to a computer system or via a cable connection. The server 1306 can host the methods to translate received data into sleep results i.e., sleep stages (hypnograms) and sleep events (e.g., apnea detection, sleep walking, snoring). Examples of hypnograms are shown in chart 1310. In some implementations, raw sensor data is provided to the server 1306. In other implementations, to conserve power and manage bandwidth constraints, the BDR 1302 may perform at least some of the processing of the heart beat data, which reduces the amount of data that must be transferred.

The methods to generate sleep results and reports can be housed on the computer system. They can additionally or alternatively be hosted on or communicated to the mobile application of the mobile device 1304 or even on the BDR 1302. In consumer applications, the results i.e., hypnograms, long term views, sleep events etc. can be displayed daily and over long periods of time for the subject to view along with their Sleep Score, Subjective Sleep Score and any other sub-scores. These can be also be plot against performance and habits to enable the subject to identify trends in their sleep and correlations between different sleep variables (e.g., total sleep time vs coffee intake). In a clinical use of some implementations, the system may be prescribed to the subject by a clinician to be used for a certain period of time, usually multiple nights (e.g., 7-10 days). The subject can take the system to their home environment, or elsewhere, and wear the device while sleeping and interact with the app. The data is processed by the mobile application and uploaded to the server over the communications link, where the data is converted into a clinical report that is delivered to the clinician's office. The report can include adherence tracking to assist in behavior changes and therapy and efficacy tracking.

The wearable device can also be worn beyond sleep sessions or even all day, where coupled with analytical processes, activity and performance can also be monitored. In some implementations, occurrences of stress and anxiety are also detected and scored. Stress and anxiety can be distinguished from high intensity physical exercise using a combination of HRV analysis and neural networks. For specific cases such as developmental disorders, patterns such as rocking, seizures etc. can be detected and even mapped by time and location when location systems are available to the analytics.

A number of implementations have been described. Nevertheless, it will be understood that various modifications may be made without departing from the spirit and scope of the disclosure. For example, various forms of the flows shown above may be used, with steps re-ordered, added, or removed.

Embodiments of the invention and all of the functional operations described in this specification can be implemented in digital electronic circuitry, or in computer software, firmware, or hardware, including the structures disclosed in this specification and their structural equivalents, or in combinations of one or more of them. Embodiments of the invention can be implemented as one or more computer program products, e.g., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the invention can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the invention, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

Particular embodiments of the invention have been described. Other embodiments are within the scope of the following claims. For example, the steps recited in the claims can be performed in a different order and still achieve desirable results.

What is claimed is:

1. A method performed by one or more computing devices, the method comprising:

accessing, by the one or more computing devices, sleep stage data generated from sensor data measured during one or more sleep sessions of a particular person, wherein the sleep stage data indicates periods of the one or more sleep sessions and corresponding sleep stages of the particular person during the one or more sleep sessions, wherein the one or more computing devices comprise a user device, and the sensor data comprises data generated by a body data recorder worn by the particular person during the one or more sleep sessions;

determining, by the one or more computing devices, a sleep quality score based on analysis of the one or more sleep sessions, wherein determining the sleep quality score comprises:

identifying, from among multiple segments of the one or more sleep sessions that are designated as rapid eye movement (REM) stages, a longest REM segment;

identifying, from among multiple segments of the one or more sleep sessions that are designated as slow wave sleep (SWS) stages, a longest SWS segment;

determining a REM score representing characteristics of REM stages of the particular person during the one or more sleep sessions, wherein the REM score is determined based on (i) a total duration of the multiple segments designated as REM stages for the one or more sleep sessions and (ii) a duration of the longest REM segment that has been identified as the longest of the multiple segments designated as REM stages, wherein determining the REM score is further based on determining, for each of the one or more sleep sessions, whether segments of the sleep session that are designated as REM stages have increasing lengths as the sleep session progresses;

determining a SWS score representing characteristics of deep sleep of the particular person during the one or more sleep sessions, wherein the SWS score is determined based on (i) a total duration of the multiple segments designated as SWS stages for the one or more sleep sessions and (ii) a duration of a longest SWS segment that has been identified as the longest of the multiple segments designated as SWS stages; and determining the sleep quality score based at least on the REM score and the SWS score;

generating, by the one or more computing devices, data for a visual representation of the sleep stages of the one or more sleep sessions, wherein the visual representation includes elements indicating a progression of the sleep stages over time during the one or more sleep sessions;

displaying, by the one or more computing devices, the visual representation on a display of the user device; and displaying, by the one or more computing devices, an indication of the determined sleep quality score on the display of the user device.

2. The method of claim 1, wherein accessing the data comprises accessing data indicating sleep stages of multiple different sleep sessions of the particular person;
wherein generating the data for the visual representation comprises generating data for a visual representation of the multiple different sleep sessions, wherein the visual representation includes, for each sleep session, a ribbon having a sequence of horizontal elements indicating a progression of the sleep stages over time during the sleep session, wherein the ribbons for the multiple sleep sessions are arranged in a column.

3. The method of claim 2, wherein the ribbons for the multiple sleep sessions are horizontally aligned so that (i) a same horizontal position indicates a same time of day for each of the sleep sessions, or (ii) a same horizontal position indicates a start of each of the sleep sessions; and
wherein the visual representation is configurable by a user of the user device to change a number of sleep sessions indicated in the visual representation, and horizontal alignment can be changed to view multiple sleep sessions, sleep architectures, or sleep signatures.

4. The method of claim 1, wherein the elements are sized according to respective durations of time periods of the one or more sleep sessions corresponding to the elements, and each of the elements is color-coded to indicate the sleep stage of the corresponding period;
wherein the sleep stages include a wake stage, a rapid eye movement (REM) stage, and two or more different types of non-REM stages of sleep.

5. The method of claim 1, wherein generating the data for the visual representation of the sleep stages comprises generating data for a visual representation that includes indicators of events occurring during the one or more sleep sessions, the indicators being aligned relative to the elements to indicate, with respect to the elements, times that the events occurred, wherein the indicators are indicators of sleep apnea events.

6. The method of claim 1, further comprising accessing second sleep stage data generated from second sensor data measured during one or more second sleep sessions of a second person that is different from the particular person, wherein the second sleep stage data indicates periods of the one or more second sleep sessions and corresponding sleep stages of the second person during the one or more second sleep sessions;
wherein generating the data for the visual representation comprises generating data for a visual representation that includes:
the elements indicating the progression of the sleep stages over time during the one or more sleep sessions of the particular person; and
elements indicating a progression of the sleep stages over time during the one or more second sleep sessions of the second person.

7. The method of claim 1, further comprising determining a sleep onset latency score for the one or more sleep sessions indicating an amount of time between a wake stage and a first sleep stage that occurs after the wake stage;
wherein the sleep quality score is determined based on the sleep onset latency score.

8. The method of claim 1, further comprising determining a cumulative sleep score based on a sum of durations of segments of the one or more sleep sessions designated as REM stages and durations of segments designated as slow wave sleep segments;
wherein the sleep quality score is further based on the cumulative sleep score.

9. The method of claim 1, further comprising determining a number of events of a particular type that occurred during the one or more sleep sessions, and durations of the events, wherein the particular type is a snoring event or an apnea event, wherein the number and duration of the events is determined based on audio data generated using a microphone of the body data recorder or the user device.

10. The method of claim 1, further comprising:
determining a sleep onset time for a particular sleep session;
determining a final wake segment in the particular sleep session; and
determining a Wake After Sleep Onset (WASO) score as a sum of all segment durations for segments of the particular sleep session designated as wake segments, excluding segments before the sleep onset time and the final wake segment.

11. The method of claim 10, further comprising:
determining a relative sleep duration score based on a total time the particular person is in non-wake sleep stages during the one or more sleep sessions; and
determining a general sleep score as a geometric mean of at least the WASO score and the total sleep time score;
wherein the sleep quality score is further based on the general sleep score.

12. The method of claim 11, wherein the WASO Score is a number that decays in a Gaussian trend as the time awake after sleep onset increases; and
wherein the relative sleep duration score is based on an amount of sleep that occurred during the one or more sleep sessions relative to a target amount of sleep.

13. The method of claim 1, further comprising determining a stage occurrence score for the one or more sleep sessions indicating a number of occurrences of a particular sleep stage or transitions to or from the particular sleep stage in the one or more sleep sessions;
wherein the sleep quality score is determined based on the stage occurrence score.

14. The method of claim 1, wherein determining the SWS score is further based on an amount of SWS sleep determined to be completed within an initial four hours after sleep onset during the respective sleep sessions of the one or more sleep sessions.

15. The method of claim 1, further comprising providing, on a user interface of an application running on the user device, a reaction time test to measure the reaction time of the particular person following a sleep session; and
displaying, on the display of the user device, an indication of the measured reaction time.

16. The method of claim 15, further comprising determining one or more relationships between the results of the reaction time test and one or more sleep metrics, the reaction time test being administered at different times and after different sleep sessions;
identifying relationships between results of the reaction time test and the one or more sleep metrics and providing one or more measures of the identified relationships on the display of the user device.

17. The method of claim 1, further comprising analyzing sleep metrics determined for multiple sleep sessions to track a sleep debt of the user accrued over the multiple sleep sessions; and generating data indicating likelihoods of adverse outcomes using sleep architectures indicating patterns of sleep stages within the multiple sleep sessions and scores for the sleep sessions.

18. The method of claim 1, wherein determining the REM score comprises determining a weighted combination of (i) a REM total duration score based on the total duration of the multiple segments designated as REM stages, and (ii) a REM longest segment score based on the duration of the longest REM segment; and wherein determining the SWS score comprises determining a weighted combination of (i) a SWS total duration score based on the total duration of the multiple segments designated as SWS stages, and (ii) a SWS longest segment score based on the duration of the longest SWS segment.

19. The method of claim 1, comprising wherein the REM score is determined based on a measure of an extent that successive REM stages increase in duration over a sleep session.

20. The method of claim 19, comprising determining a REM ascending factor score by computing differences in durations of the successive REM stages over the sleep session, wherein the REM score is based on the REM ascending factor score.

21. One or more non-transitory computer-readable media storing instructions that, when executed by one or more computing devices, cause the one or more computing devices to perform operations comprising:

accessing, by the one or more computing devices, sleep stage data generated from sensor data measured during a particular sleep session of a particular person, wherein the sleep stage data indicates periods of the particular sleep session and corresponding sleep stages of the particular person during the particular sleep session, wherein the one or more computers comprise a user device, and the sensor data comprises data generated by a body data recorder worn by the particular person during the particular sleep session;

identifying, from among multiple segments of the particular sleep session that are designated as rapid eye movement (REM) stages, a longest REM segment;

identifying, from among multiple segments of the particular sleep session that are designated as slow wave sleep (SWS) stages, a longest SWS segment;

determining, by the one or more computing devices, a REM score representing characteristics of REM stages of the particular person during the particular sleep session, wherein the REM score is determined based on (i) a total duration of the multiple segments designated as REM stages for the particular sleep session and (ii) a duration of the longest REM segment that has been identified as the longest of the multiple segments designated as REM stages, wherein determining the REM score is further based on determining whether segments of the particular sleep session that are designated as REM stages have increasing lengths as the particular sleep session progresses;

determining, by the one or more computing devices, a SWS score representing characteristics of deep sleep of the particular person during the particular sleep session, wherein the SWS score is determined based on (i) a total duration of the multiple segments designated as SWS stages for the particular sleep session and (ii) a duration of a longest SWS segment that has been identified as the longest of the multiple segments designated as SWS stages;

determining, by the one or more computing devices, a sleep quality score for the particular sleep session based at least on the REM score and the SWS score;

generating, by the one or more computing devices, data for a visual representation of the sleep stages of the particular sleep session, wherein the visual representation includes elements indicating a progression of the sleep stages over time during the particular sleep session;

displaying, by the one or more computing devices, the visual representation of the visual representation of the sleep stages of the particular sleep session on a display of a user device; and displaying, by the one or more computing devices, an indication of the determined sleep quality score for the particular sleep session on the display of the user device.

22. The one or more non-transitory computer-readable media of claim 21, wherein the operations comprise determining, by the one or more computing devices, a general sleep score for the particular sleep session based on (i) a Wake After Sleep Onset (WASO) score as a sum of all segment durations for segments of the particular sleep session designated as wake segments, excluding segments before a sleep onset time and a final wake segment of the particular sleep session and (ii) a relative sleep duration score based on a total time the particular person is in non-wake sleep stages during the particular sleep session relative to a target amount of sleep;

wherein determining the sleep quality score for the particular sleep session is based at least on the REM score, the SWS score, and the general sleep score.

23. A system comprising:
one or more processors; and
one or more computer-readable media storing instructions that, when executed by the one or more processors, cause the system to perform operations comprising:

accessing sleep stage data generated from sensor data measured during one or more sleep sessions of a particular person, wherein the sleep stage data indicates periods of the one or more sleep sessions and corresponding sleep stages of the particular person during the one or more sleep sessions, wherein the one or more processors comprise one or more processors of a user device, and the sensor data comprises data generated by a body data recorder worn by the particular person during the one or more sleep sessions;

determining a sleep quality score based on analysis of the one or more sleep sessions, wherein determining the sleep quality score comprises:

identifying, from among multiple segments of the one or more sleep sessions that are designated as rapid eye movement (REM) stages, a longest REM segment;

identifying, from among multiple segments of the one or more sleep sessions that are designated as slow wave sleep (SWS) stages, a longest SWS segment;

determining a REM score representing characteristics of REM stages of the particular person during the one or more sleep sessions, wherein the REM score is determined based on (i) a total duration of the multiple segments designated as REM stages for the one or more sleep sessions and (ii) a duration of the longest REM segment that has been identified as the longest of the multiple segments designated as REM stages, wherein determining the REM score is further based on determining, for each of the one or more sleep sessions, whether segments of the sleep session that are designated as REM stages have increasing lengths as the sleep session progresses;

determining a SWS score representing characteristics of deep sleep of the particular person during the one or more sleep sessions, wherein the SWS score is determined based on (i) a total duration of the multiple segments designated as SWS stages for the one or more sleep sessions and (ii) a duration of a longest SWS segment that has been identified as the longest of the multiple segments designated as SWS stages; and determining the sleep quality score based at least on the REM score and the SWS score;

generating data for a visual representation of the sleep stages of the one or more sleep sessions, wherein the visual representation includes elements indicating a progression of the sleep stages over time during the one or more sleep sessions;

displaying the visual representation on a display of the user device; and displaying an indication of the determined sleep quality score on the display of the user device.

\* \* \* \* \*

UNITED STATES PATENT AND TRADEMARK OFFICE
CERTIFICATE OF CORRECTION

PATENT NO. : 10,582,890 B2
APPLICATION NO. : 15/249032
DATED : March 10, 2020
INVENTOR(S) : Bandyopadhyay et al.

It is certified that error appears in the above-identified patent and that said Letters Patent is hereby corrected as shown below:

In the Claims

Column 26, Line 56, Claim 16, after "between" delete "the".

Signed and Sealed this
Second Day of June, 2020

Andrei Iancu
*Director of the United States Patent and Trademark Office*